(12) United States Patent
Caires et al.

(10) Patent No.: US 7,432,403 B2
(45) Date of Patent: Oct. 7, 2008

(54) CYCLIC PALLADIUM COMPOUNDS HAVING COORDINATED THERETO BIS (DIPHENYLPHOSPHINE) FERROCENE LIGANDS WHICH INHIBIT THE ACTIVITY OF PROTEINS AND ENZYMES AND TREATMENT OF DISEASES AND DISORDERS ASSOCIATED THEREWITH

(75) Inventors: Antonio Carlos Fávero Caires, Mogi das Cruzes (BR); Claudia Bincoletto Trindade, Mogi das Cruzes (BR); Ivarne Luis dos Santos Tersariol, Mogi das Cruzes (BR)

(73) Assignee: Fundação De Amparo À Pesquisa Do Estado de São Paulo, São Paulo (BR)

( * ) Notice: Subject to any disclaimer, the term of this patent is extended or adjusted under 35 U.S.C. 154(b) by 30 days.

(21) Appl. No.: 10/525,781

(22) PCT Filed: Aug. 22, 2003

(86) PCT No.: PCT/BR03/00120

§ 371 (c)(1),
(2), (4) Date: Sep. 20, 2005

(87) PCT Pub. No.: WO2004/019924

PCT Pub. Date: Mar. 11, 2004

(65) Prior Publication Data

US 2006/0106100 A1    May 18, 2006

(30) Foreign Application Priority Data

Aug. 30, 2002 (BR) .................................... 0204160

(51) Int. Cl.
*C07C 45/50* (2006.01)
*C07F 15/00* (2006.01)
(52) U.S. Cl. ...................................... 568/454; 514/492
(58) Field of Classification Search .................. None
See application file for complete search history.

(56) References Cited

U.S. PATENT DOCUMENTS

| | | | | |
|---|---|---|---|---|
| 4,584,316 A | * | 4/1986 | Rosenberg et al. | 514/492 |
| 5,618,983 A | * | 4/1997 | Burke | 568/454 |
| 5,880,149 A |   | 3/1999 | Grinstaff et al. | |

OTHER PUBLICATIONS

Ananias et al. Transition Metal chemistry 26(4-5). 2001. 570-573.*
Ares, Raquel, et al., "Functionalized cyclopalladated compounds with bidentateGroup 15 donor atom ligands: the crystaland molecular structures of [{Pd[5-(COH)C$_6$H$_3$C(H)=NCy-C2,N](C1)}$_2$(μ-Ph$_2$PRPPh$_2$)] (R = CH$_2$CH$_2$, Fe(C$_5$H$_4$)$_2$], [Pd {5-(COH)C$_6$H$_3$C(H)=NCy-C2,N}(Ph$_2$PCH$_2$PPh$_2$-P,P)][PF$_6$] and [Pd{5-(COH)C$_6$H$_3$C(H)=N(Cy)-C2,N}(Ph$_2$PCH$_2$CH$_2$AsPh-P,As)][PF$_6$]", Journal of Organometallic Chemistry, 665(1-2):76-86 (2003).

Ares, Raquel, et al., "Cyclopalladated compounds with bridging and chelating diphosphine ligands Effect of ring size. Crystal and molecular structure of [{Pd[4-(COH)C$_6$H$_3$C(H)=N(Cy)-C2,N] (C1)}$_2$(μ-Ph$_2$PCH$_2$PPh$_2$)]" Polyhedron, 21(22):2309-2315 (2002).

Fernandez, Alberto, et al., "The first crystal and molecular structure of a syn-acetato-bridged dinuclear cyclometallated complex ]Pd {2,3,4-(Me0)$_3$C$_6$HC(H)=NCH$_2$CH$_2$OH}-(μ-OAc)]$_2$", Eur. J. Inorg. Chem., 9:2389-2401 (Sep. 2002).

Fernandez, Alberto, et al., "Cyclopalladated compounds derived from a [C,N,S] terdentate ligand: synthesis, characterization and reactivity. Crystal and molecular structures of [Pd{2-CIC$_6$H$_3$C(H)=NCH$_2$CH$_2$SMe}(C1)] and {Pd[2-ClC$_6$H$_3$C(H)=NCH$_2$CH$_2$SMe]}$_2$ {μ-Ph$_2$P(CH$_2$)$_4$PPh$_2$}]-CF$_3$SO$_3$]$_2$" New J. Chem., 26(1):105-112 (Jan. 2002).

Vila, Jose M., et al., "Novel cyclopalladated ferrocenyl Schiff base compounds with bridging and chelating diphosphines. Crystal and molecular structure of [{Pd [(η$^5$-C$_5$H$_5$)Fe(η$^5$-C$_5$H$_3$)C(H):N-2,4,6-Me$_3$C$_6$H$_2$]}-Ph$_2$P(CH$_2$)$_n$PPh$_2$-P,P}][PF$_6$] (n = 1,2)", Journal of Organometallic Chemistry, ( 637-639): 577-585 (Dec. 2001).

Castro-Juiz, Samuel, et al., "Directed regioselectivity in cyclometallated palladium(II) compounds of N-benzyl1denebenzylamines. Crystal and molecular structure of [Pd{3,4-(OCH$_2$O)C$_6$H$_2$C(H)=NCH$_2$-[3,4-(OCH$_2$O)C$_6$H$_3$]-C2,N}(μ-O$_2$CMe)]$_2$", Polyhedron, 20:2925-2933 (2001).

Ananias, Sandra R., et al., "Cleavage of the dimeric cyclopalladated IPd(N,C-dmba)(μ.-X) I$_2$, (dmba = N,N-dimethylbenzylamine; X = SCN and NCO) by diphosphines. Palladium(II) compounds with distinct structures in the solid-state and in solution",Transition Metal Chemistry, 26(4-5): 570-573 (Dordrecht, Netherlands: 2001).

Lousame, Mariela, et al., "Synthesis and single-crystal X-ray diffraction studies of new cyclometallated phenylimidazole palladium (II) compounds", Eur. J. Inorga. Chem., 9:2055-2062 (Sep. 2000).

Ma, Jian-Fang, et al., "Reaction of *di-μ*.-dichloro-bis(N,N-dimethylbenzylamine- C$^2$,N)dipalladium(II) with diphosphines. Six-membered ring complexes bearing spiro rings", Inorganica Chimica Acta, 299(2): 164-171 (Mar. 2000).

Boehm, Andreas, et al., "Metal complexes of biologically important ligands. Part 104. Ortho-palladated complexes of N,N-dimethyl(phenyl)glycine methyl ester. Synthesis of.alpha.-amino acid derivatives by insertion of isocyanides, CO, alkenes, and alkynes into the Pd-C bond", Zeitschrift Fuer Naturforschung, B Chemical Sciences, 53(4):448-458 (1998).

(Continued)

*Primary Examiner*—Yvonne Eyler
*Assistant Examiner*—Louisa Lao
(74) *Attorney, Agent, or Firm*—Volpe and Koenig P.C.

(57) ABSTRACT

The invention relates to cyclopalladated compounds containing bis-diphenyiphosphine-ferrocene ligands and their analogues which are active inhibitors of proteins and enzymes, for example, those of the serine peptidase, cysteine-protease, metalo-protease and endopeptidase families, involved in the development and metastases of malignant tumors, e.g. of the thyroid. An exemplary compound is shown in the figure. The compounds are able te modulate the immunological system due to their action on the enzymes and their interaction with DNA molecules.

6 Claims, 11 Drawing Sheets

OTHER PUBLICATIONS

Zhao, Gang, et al., "Optically active cyclopalladated derivatives of arylimines. Crystal structures of (+)-[{Pd[p-MeOC$_6$H$_3$CH=NCH$_2$-(1S,2R,5S)-CHCH$_2$CH$_2$CHC(Me)$_2$CHCH$_2$](μ-X}$_2$ (X = Cl or Br), (+)-[Pd{p-MeOC$_6$H$_3$CH=NCH$_2$-(1S,2R,5S)-CHCH$_2$-CH$_2$CHC(Me)$_2$CHCH$_2$}Cl(PPh$_3$)] and (+)-[{Pd[p-MeOC$_6$H$_3$CH=NCH$_2$-(1S,2R,5S)-CHCH$_2$CH$_2$CHC(Me)$_2$CHCH$_2$]Cl}$_2$-{Fe(η$_5$H$_4$PPh$_2$)$_2$}]," J. Chem. Soc., Dalton Transactions: Inorganic Chemistry, 7:1241-1247 (1998).

Zhao, Gang, et al., "DiastereoselectiveCyclopalladation of New Chiral Ferrocenylimines (−)-[(η$^5$-C$_5$H$_5$)Fe{η.5-C$_5$H$_4$C(R)=NCH$_2$-(1S,2R,5S)- CHCH$_2$CH$_2$CHC(CH$_3$)$_2$CHCH$_2$}]. Crystal Structures of (Sp)-[Pd{(η$^5$-C$_5$H$_3$C(R)=NCH$_2$-(1S,2R,5S)-CHCH$_2$CH$_2$CHC(CH$_3$)$_2$CHCH$_2$)Fe(η5-C$_5$H$_5$)}(PPh$_3$)Cl] (R = H or Me)", Organometallics 16(18): 4023-4026 (1997).

Quiroga, A. G., et al., "Novel tetranuclear orthometalated complexes of Pd(II) and Pt(II) derived from p-iospropylbenzaldehyde thiosemicarbazone with cytostatic actitivy in cis-DDP resistant tumor line cells. Interaction of these complexes with DNA", J. Med. Chem., 41(9): 1399-1408 (Apr. 1998).

Navarro-Ranninger, Carmen, et al., "Cyclometalated complexes of platinum and palladium with N-(4-chlorophenyl)-alpha-benzoylbenzylideneamine. In vitro cytostatic activity, DNA modification and interstrand cross-link studies", Inorg. Chem. 35(18): 5181-5187 (Aug. 1996).

Navarro-Ranninger, C., et al., "Analysis of two cycloplatinated compounds derived from N-(4-methoxyphenyl)-alpha-benzoylbenzylidenamide: Comparison of the activity of these compounds with other isostructural cyclopalladated compounds", J. Med. Chem. 36(24): 3795-3801 (Nov. 1993).

Caires—Synthesis and Cytotoxicity of Some Cyclometallated Palladium(II) Complexes Containing Coordinated Azide and Diphosphines—Quimica Nova, 22(3) (1999) pp. 329-334.

Barbosa et al., Biphosphinic palladacycle complex mediates lysosomal-membrane permeabilization and cell death in K562 leukaemia cells—European Journal of Pharmacology 542 (2006) 37-47.

Bincoletto et al., Chiral cyclopalladated complexes derived from N,N-dimethyl-1-phenethylamine with bridging bis(diphenylphosphine)ferrocene ligand as inhibitors of the cathepsin B activity and as antitumoral agents—Bioorganic & Medicinal Chemistry 13 (2005) 3047-3055.

Caires, A.C.F., Recent Advances Involving Palladium (II) Complexes for the Cancer Therapy—Anti-Cancer Agents in Medicinal Chemistry, 2007, vol. 7, No. 5, pp. 1-8—2007 Bentham Science Publishers Ltd.

Rodrigues et al., Cyclopalladated Compounds As Chemotherapeutic Agents: Antitumor Activity Against A Murine Melanoma Cell Line—Int. J. Cancer: 107, 498-504 (2003).

* cited by examiner

CYCLIC PALLADIUM COMPOUNDS HAVING COORDINATED THERETO BIS (DIPHENYLPHOSPHINE) FERROCENE LIGANDS WHICH INHIBIT THE ACTIVITY OF PROTEINS AND ENZYMES AND TREATMENT OF DISEASES AND DISORDERS ASSOCIATED THEREWITH

FIELD OF THE INVENTION

The invention refers to cyclopalladated compounds containing bis-diphenylphosphine-ferrocene coordinated ligands and their analogues as active inhibitors for peptides and enzymes comprising serine peptidase, cysteine-protease, metallo-protease and endopeptidase families, many of which are essential for the route of growth and metastasis of malignant tumors. Acting over these enzymes and taking part of insertions with DNA molecules, these compounds modulate the immunological system.

BACKGROUND

The study of inorganic chemistry in the pharmaceutical field has been receiving special attention from researchers due to the clear advantages of its use over traditional medicines for the treatment of a series of pathologies.

The best-studied inorganic pharmaceutical is cisplatin, a drug which has been clinically used for the treatment of a wide range of tumors. It is believed that its action occurs by means of interaction with DNA, thus inhibiting the proliferation of tumor cells (Lippard, *Science* 218: 1075-1082 (1982); Rosenberg, *Nature* 222: 385 (1969); Cleare et al, *Bioinorg. Chem.* 2: 187 (1973)). This compound is efficient for the combat against various kinds of tumors and is highly cytotoxic, being also extensive to normal cells (Ebert, U., Loffler, H., Kirch, W., *Pharmacology & Therapeutics,* 74: (2) 207-220 1997; Spencer C. M., Goa K. L., *Drugs,* 50: (6) 1001-1031 December 1995).

Gold-based complexes have been used for the treatment of arthritis and its route of action involves the linkage to a thiol group of proteins, thus inhibiting the appearance of disulphite bridges, which may cause their denaturation.

Metal complexes of cobalt have also been already pointed out as presenting antiviral, antitumor and antimicrobial activity, besides anti-inflammatory properties.

Metal compounds which can change or link to functional sites of proteins resulting in the inactivation of its biological activities are described by the U.S. Pat. No. 5,880,149. The document discloses some palladium complexes (pertaining to the class of coordination compounds), as irreversible inhibitors of cysteine-proteases, as powerful antitumor drugs and as very efficient drugs in numerous infectious processes, in which the route of action of cysteine-proteases is involved. As an example, we mention the enzymatic inhibition caused by palladium complexes over Cathepsins B, H, J, L, N, S, T and C and over the Interleukine Converter Enzyme (ICE), constituting active drugs against Amebiasiss, Trypanosomiasis and Leishmaniosis. The U.S. patent is the latest work published on the development and routes of action of antitumor drugs, involving compounds of the chemical element palladium.

FERNANDEZ, Alberto et al: "Cyclopalladated compounds derived from a 'C,N,S! terdentate ligand: synthesis, characterization and reactivity. Crystal and molecular structure of 'Pd{2-ClC6H3C(H); NCH2CH2SMe}(Cl)! and 'Pd{2-ClC6H3C(H); NCH2CH2SMe!} 2{mu,-Ph2P(CH2)4PPh2}!'CF3SO3!2",New Journal of Chemistry, (Jan. 25, 2002), 26(1), 105-112, XP009020790-ISSN: 1144-0546, purely refers to the synthesis and reactivity of the cyclopalladated compounds containing halogens. It does not have any similarity to the application and its biological effects. Despite containing a biphosphinic ligand in bridge, as in the invention, there is a great structural difference between compound 7 reported and the structures of the application. The difference lies on the fact that the nitrogen atom linked to the palladium has a double connection [—N(SMe)=C(H)—] which is not the case of the structures mentioned in the invention. This fact, allied to the fact that the same atom of nitrogen possesses an —SMe ligand, gives these compounds another type of reactivity, among which, the possibility of formation of tridentate complexes involving (C, N, S).

VILA, Jose M. et al: "Novel Cyclopalladated ferrocenyl Schiff base compounds with bridging and chelating diphosphines. Crystal and molecular structure of [{Pd(eta,5-C5H5) Fe (eta, 5-C5H3)C(H):N-2,4,6-Me3C6H2]}-{Ph2P(CH2) nPPh2-P,P}][PF6](n=1,2)" Journal of Organometallic Chemistry (Mar. 12, 2001), 637-639, 577-585 XP004323943-ISSN: 0022-328X, like the previous one, it has a fundamental structural difference in relation to the invention compounds. The researcher considers Shiff Bases as metallation agents on the palladium. That gives a double connection to the nitrogen linked to the metal, as in the CpFe(C6H4)—C=NR—Pd cycle. In the invention, the requested metallation agent does not have this characteristic. In the case of ionic compounds the invention does not mention the $PF_6^-$ ion.

CASTRO-JUIZ, Samuel et al: "Directed regioselectivity in cyclometallated palladium(II) compounds of N-Benzylidenebenzylamines. Crystal and molecular structure of [Pd{3,4-(OCHO)C6H2C(H)=NCH2-[3,4-(OCHO)C6H3] C2,N}(um-O2CMe)}2", Polyhedron (15 Nov. 2001), 20(24-25), 2925-2933, XP 002261131-ISSN: 0277-5387, and also in the case of N-Benzylidenebenzylamines, that contain an atom of nitrogen with double connection, and are used here as a metallation agent, there is the fundamental difference of structures of the patent document, where Y clearly represents an atom of the group V or VI of the periodic table, where the double connection is absent. The patent application shows the potential use of the palladacycle compounds as antitumoral agents since they inhibit, mainly, the cathepsin-B enzyme, which the inventors have discovered. None of this was reported by this document.

ANANIAS, Sandra R. et al: "Cleavage of the dimeric cyclopalladated [Pd(N,C-dmba)(µ-X)]₂, (dmba=N,N-dimethylbenzylamine; X=SCN and NCO) by diphosphines. Palladium(II) compounds with distinct structures in the solid-state and in solution", Transition Metal Chemistry (Dordrecht, Netherlands), (2001), 26(4,5), 570-573, XP009020786-ISSN: 0340-4285; this work of pure synthesis and palladacycle reactivity containing pseudo-halides and the metallation agent N,N-dimethylbenzylamine. Although it also involves the 1,1'-bis(difenilfosfina)ferroceno ligand in structures similar to the invention, the ligand used does not have a chiral carbon atom like in the case of the ligand that the invention has used, i.e., the N,N-dimethil-1-phenethylamine, the main compound protected in the document. Also, this document does not mention any biological effect resulting from the action of this compound on enzyme inhibition, which results in their action as antitumoral agents, the main scope of the present invention.

LOUSAME, Mariela et al: "Synthesis and single-crystal X-ray diffraction studies of new cyclometallated phenylimidazole palladium(II) compounds", European Journal of Inorganic Chemistry, (September 2000), (9), 2055-2062 XP002261132-ISSN: 1434-1948, where the author uses phenylimidazole as a cyclomettalation agent. Also, this ligand, like the N-Benzylidenebenzylamines, contains an atom of nitrogen with double connection, which is different from the invention compounds. Therefore, there is a fundamental difference in the structures reported in the invention, where Y clearly represents an atom of the V or VI group of the periodic table, where the double connection is absent. The patent application shows the potential use of the palladacycle compounds as antitumoral agents since they inhibit, mainly, the cathepsin-B enzyme. None of this was reported by the document.

MA, Jian-Fang et al: "Reaction of di-.mü.-dichloro-bis(N, N-dimethylbenzylamine-C2,N) dipalladium(II) with diphosphines. Six-member ring complexes bearing spiro rings", Inorgânica Chimica Acta (Mar. 15, 2000), 299(2), 164-171, XP002261133-ISSN: 0020-1693; work of pure synthesis and cyclopalladated reactivity containing halides and the metallation agent N,N-dimetilbenzilamina. Although it also involves the 1,1'-bis(difenilfosfina)ferroceno ligand in structures similar to the invention, t, the ligand used does not have a carbon quiral like the ligand that the invention has used, i.e., the N,N-dimetil-1-fenetilamina, main compound protected in the document. Also, this document does not mention any biological effect resulting from the action of this compound on the inhibition of enzymes, which results in their action as antitumoral agents, the main scope of the present invention BOEHM, Andreas et al: "Metal complexes of biologically important ligands. Part 104. Ortho-palladated complexes of N,N-dimethyl(phenyl)glycine methyl esther. Synthesis of .alpha.-amino acid derivatives by insertion of isocyanides, CO, alkenes, and alkynes into the Pd—C bond" Zeitschrift Fuer Naturforschung, B:, Chemical Sciences, (1998), 53(4), 448-458 XP009020783 ISSN: 0932-0776, wich does not have any similarity to the invention or its biological effects. Work of pure synthesis and reactivity of palladacycle containing halides and N,N-dimethilbenzylamine metallation agent. Although it also involves the 1,1'-bis(difenilfosfina) ferroceno ligand in structures similar to the invention, the ligand used does not have a chiral carbon like the ligand used by us, i.e., the N,N-dimetil-1-fenetilamina, main compound protected in the document. The document does not mention any biological effect resulting from the action of this compound on the inhibition of enzymes either, which results in their action as antitumoral agents, the main scope of the present invention.

ZHAO, Gang et al: "Optically active cyclopalladated derivatives of arylimines. Crystal structure of 'cyclic! (+)-' (Pd'p-MeOC6H3CH; NCH2-(1S,2R5S)-CHCH2CH2CHMe2CHCH2!(.mu.-X)}2! (X=Cl or Br), 'cyclic!(+)-'Pd{p-MeO C6H3CH; NCH2-(1S,2R,5S)-CHCH2CH2CHMe2CHCH2}Cl(PPh3)! and 'cyclic!(+)-Pd{p-MeO C6H3CH; NCH2-(1S,2R5S)-CHCH2CH2CHMe2CHCH2]Cl}2-{Fe(eta-5H4PPh2)2]}" Journal of the Chemical Society, Dalton Transactions: Inorganic Chemistry (1998), (7), 1241-1247 XP-002261134-ISSN: 1472-7773; is also restricted to the synthesis and structural characterization of palladacycle compounds with optical isomeric with the biphosphinic ligand identical to the invention, i.e., the 1,1'-bis(diphenylphosphine)ferrocene. Besides, it must be pointed out once more that it uses a cyclometallation agent that, like the N-Benzylidenebenzylamines and the phenylimidazole previously mentioned, contains an atom of nitrogen with double connection, different from the invention compounds. Thus, there is a fundamental difference between the structures, where Y clearly represents an atom of the V or VI group of the periodic table, where the double connection is absent. The present invention shows the potential use of the palladacycle compounds as antitumoral agents since they inhibit, mainly, the cathepsin-B enzyme, which the inventors have discovered. None of this was reported by this document.

ZHAO, Gang et al: "Diastereoselective Cyclopalladation of New Chiral Ferrocenylimines (–)-'(,eta,5-C5H5) Fe {,eta, 5-C5H4C (R;NCH2-(1S,2R,5 S)-CHCH2CH2CHC(CH3) 2CHCH2}!. Crystal structures of (Sp-'Pd{(,eta,5-C5H3C (R): NCH2-(1S,2R,5S)-CHCH2CH2CHC(CH3) 2CHCH2) Fe(.eta.5-C5H5)}(PPh3) Cl! (R=H or Me)" Organometallics (Feb. 7, 1997), 16(18), 4023-4026 XP002261135-ISSN: 0276-7333, which is also restricted to the synthesis and structural characterization of palladacycle compounds with optical isomery with the biphosphinic ligand identical to the invention, i.e., the 1,1'-bis(diphenylphosphine) ferrocene. Furthermore, it must be stressed that this document uses a cyclometallation agent that, like the N-Benzylidenebenzylamines and the phenylimidazole previously mentioned, contains an atom of nitrogen with double connection, different from the invention compounds. Thus, there is a fundamental difference in the structures presented in the patent document, where Y clearly represents an atom of the group V or VI of the periodic table, where the double connection is absent. The present invention shows the potential use of the palladacycle compounds as antitumoral agents since they inhibit, mainly, the cathepsin-B enzyme, which the inventors have discovered. None of this was reported by the document.

QUIROGA, A. G. et al: "Novel tetranuclear orthometalated complexes of Pd(II) and Pt(II) derived from p-iospropylbenzaldehyde thiosemicarbazone with cytostatic activity in cis-DDP resistant tumor line cells. Interaction of these complexes with DNA", Journal of Medicinal Chemistry, (Apr. 23, 1998), 41(9), 1399-1408, XP002261136-ISSN: 0022-2623, shows the obtainment of tetranuclear palladacycle compounds with a structure quite different from those mentioned in the invention. It also shows the antitumoral activity of those compounds. The patent, however, is very clear regarding the need of a ligand ferrocenyl-phosphines or similar in the structure. It also claims antitumoral action for the invention compounds since they have properties that operate as enzymatic inhibitors and modulators of the immunological system, which is totally novel, according to claims of the present invention.

NAVARRO-RANNINGER, C. et al: "Cyclometalated complexes of platinum and palladium with N-(4-chlorophenyl)-alpha-benzoylbenzylideneamine. In vitro cytostatic activity, DNA modification and interstrand cross-link studies" Inorganic Chemistry (Aug. 28, 1996), 35(18), 5181-7 XP002261137-ISSN: 0020-1669, which describes the synthesis and structural characterization of cyclopalladated compounds with antitumoral activity, approaching its interaction with DNA molecules. However, it does not mention ferrocenyl-phosphine ligands and similar ones, which are the object of the invention. It does not mention enzymatic inhibition mechanisms either.

NAVARRO-RANNINGER, C. et al: "Analysis of two chloroplatinated compounds derived from N-(4-methoxyphenyl)-alpha-benzoylbenzylidenamide: Comparison of the activity of these compounds with other isostructural cyclopalladated compounds" Journal of Medicinal Chemistry (26 Nov. 1993), 36(24), 3795-3801 XP002261138-ISSN: 0022-2623 which describes the synthesis and structural characterization of cyclopalladated with antitumoral activity, approaching its interaction with DNA molecules. However, it does not mention ferrocenyl-phosphine ligands and similar ones, which are the object of the invention. It does not mention any enzymatic inhibition mechanisms either.

SUMMARY OF THE INVENTION

The invention deals with innovative palladium complexes (pertaining to the family of organometallic compounds), containing a Sigma C—PD bond and a coordination linkage Y→Pd, giving origin to an organic cycle, for which reason these compounds are designated as cyclopalladated, also known as palladacycles.

The compounds covered by the invention can be defined by the generic structures A, B or C of the Scheme 1 below:

SCHEME 1

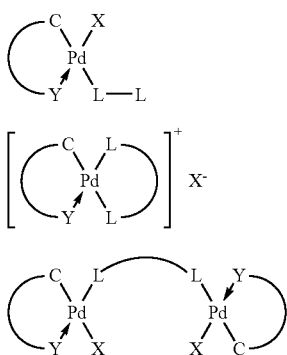

in which:

X represents an element chosen from the following groups:
1. halogen (Cl, F, Br, I);
2. pseudo-halogen ($N_3$, NCO, NCS, SCN); or
3. acetate ($H_3C$—COO—); and Y represents an element from the group V or VI of the Periodic Table, e.g. N, P, As, Sb, Bi, O, S, Se, Te;

C represents an atom of carbon with $sp^2$ or $sp^3$ hybridization, covalently linked to the atom of palladium. The ring containing C, Y and D can be constituted of three to eight atoms.

Between C and Y, represented by a curved line, there is a succession of atoms designated as cyclopalladated ring, constituted of three to eight atoms, including the atom of palladium. Typically, not excluding any other way, said atoms are chosen from carbon, nitrogen, oxygen or sulphur. Each one of these atoms constituting the ring can, on the other hand, be linked to other atoms or groupings, forming variable structures external to the ring, linear or cyclic, for which no specific limitations are known by the Applicant.

L represents a coordinated ligand which is a donating atom from the group V of the Periodic Table (N, P, As, Sb, Bi) within a bis-diphenylphosphine-ferrocene compound as detailed by Scheme 2 below, with the schematic representation L-L indicating the presence of two linkers L within the structure of said bis-diphenylphosphine-ferrocene compound, while R1, R2, R3, R4, R5, R6, R7, R8, R9, R10, R11 and R12 represent individually the following radicals, which can be present in any order: hydrogen (H), alkyl, aryl, dienyl, alkoxy, siloxy, hydroxy (OH), amino (—$NH_2$), imide, halogen (F, Cl, Br, I), imino, nitro (—$NO_2$).

SCHEME 2

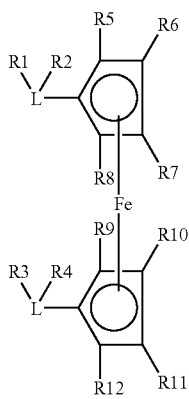

Depending on the proportion of the bis-diphenylphosphine-ferrocene ligand used for the synthesis, as well as that of the solvent, mononuclear molecular compounds (structure 1A, single-toothed cyclopalladated compound), mononuclear ionics (structure 1B, chelating bitoothed cyclopalladated compound) and binuclear molecules (structure 1C, bridged bitoothed cyclopalladated compound) can be generated. The compounds of the structures 1A and 1B are obtained when the ratio of two mol of bidentade ligand L-L to 1 mol of starting complexes is used. Compounds shown at 1C are obtained when a molar ratio of 1:1 is used.

In this work, the representation [Pd($C^2$,N-(S-dmpa)(dppf)Cl] indicates a mononuclear molecular palladium complex with the single-toothed dppf ligand as of scheme 1A, the representation [Pd($C^2$,N-(S-dmpa)(dppf)Cl] indicates an ionic mononuclear palladium complex with the dppf linker acting as a bi-toothed chelator as of scheme 1B and [$Pd_2$($C^2$, N-R+ dmpa)$_2$(μ-dppf)$Cl_2$] indicates a binuclear molecular palladium complex containing the dppf linker acting as a bridged bi-toothed linker.

In a specific embodiment of the invention, the obtained cyclopalladated compounds are represented in the Schemes 3 and 4 below, respectively derived from N,N-dimethyl-benzylamine (scheme 3) and from alkynes pyridinyl-phenyl-ethyne (scheme 4A) and 1-phenyl-3-N,N-dimethylamine-propyne (scheme 4B).

SCHEME 3

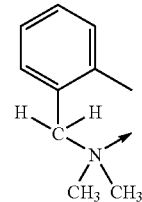

SCHEME 4A

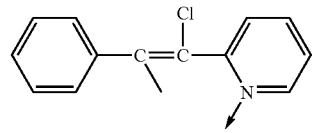

SCHEME 4B

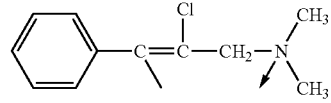

An even more particular embodiment of the invention is N,N-dimethyl-1-phenethylamine (dmpa). Scheme 5 below represents the cyclometal ring formed by the isomers of N,N-dimethyl-1-phenethylamine (dmpa)-enantiomer R(+) and enantiomer S(−).

SCHEME 5

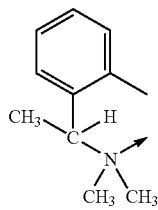

As a mere explanation, the illustrations of Schemes 3 to 5 above show the cyclopalladated ring, which should be understood as per the configuration explained in the Scheme 6 below (taking the structure of Scheme 3 as an example):

SCHEME 6

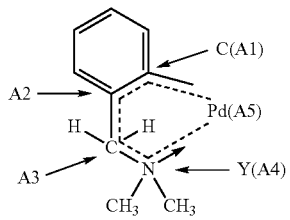

In this figure, the cyclopalladated ring comprises five atoms, indicated as A1 to A5, interlinked as previously described, i.e.:

an atom of carbon (A1) is bonded to the palladium (A5) by a sigma bond;

an atom of nitrogen (A4, generically defined as Y in the general formula) is bonded to the palladium (A5) by a covalent donor linkage;

the atom A2 is a carbon and, together with A1, are also a part of a benzene ring "external" to the cyclopalladated ring;

the atom A4 of nitrogen is linked to two ethyl radicals "external" to the cyclopalladated ring;

the atom A3 is another atom of carbon bonded to two atoms of hydrogen "external" to the cyclopalladated ring;

palladium, atom A5, is linked to a bis-diphenylphosphine-ferrocene, in which R1 to R12 are atoms of hydrogen;

The dotted part of scheme 6 shows the atoms forming the cyclopalladated ring together with the palladium.

Complementing the illustrative example, that cyclopalladated compound, together with the 1,1'-bis-diphenylphosphine-ferrocene ligand, could generate, in one of the presented possibilities, the complex structure represented as follows:

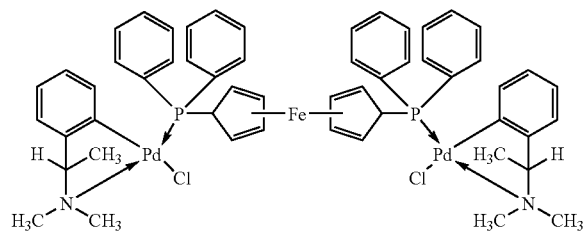

The large group of cyclopalladated compounds obtained as per the invention, especially the compounds derived from enantiomers R(+) and S(−) of the organic compound N,N-dimethyl-1-phenethylamine (triethylamine), represented by (dmpa) and containing the coordinated ligand 1,1'-bis-diphenylphosphine-ferrocene within its structures, are compounds which can present many advantages as pharmaceuticals, for the treatment of a large range of diseases.

This fact is due to the capacity of said compounds to inhibit enyzmes and proteins comprising those pertaining to both cysteine-protease (Cathepsin B) and serine peptidase (prolyl-oligopeptidase) families, as well as the Angiotensin Converting Enzyme (ACE) and Cathepsin D. Inhibitors for these enzymes or proteins by means of cyclopalladated complexes have not been previously described and, although said complexes are sintetized by known methods, the compounds containing bis-diphenylphosphine-ferrocene ligands are fully new.

The route of action of the compounds of the invention occurs in a mainly reversible way over enzymes or proteins, acting especially on the Enzyme-Substrate complex. Such reversibility implies low cytotoxicity and reduction of undesirable side effects when given as drugs, but not affecting their efficiency as pharmaceuticals.

The inhibiting effect presented by the cyclopalladated complexes over a range of enzyme groups to which e.g. Cathepsin B, prolyl-oligopeptidase family, Cathepsin D and Angiotensin Converting Enzyme (ACE) pertain, results in immunomodulation properties of these compounds. Inhibition and immunomodulation effects grant properties as anti-metastasis, antiangiogenic and involvement in cell apoptosis to cyclopalladated compounds at issue, making them become drugs, particularly for the treatment of diseases related to these proteins and, even more particularly, against solid or ascitic malignant tumors (blood and lymph system).

Cyclopalladated compounds of the invention represent pharmaceuticals for the combat against thyroid cancer, against which there is no specific chemotherapeutical so far, and neuroblastomas. This is mainly due to the inability of inhibition over Cathepsin D and protection of bone marrow cells, caused by interference between cyclopalladated compounds and the immunological system. These characteristics grant immunological protection action against undesirable secondary effects to compounds as described herein for treatments involving the use of radiotherapy.

Figure 8:
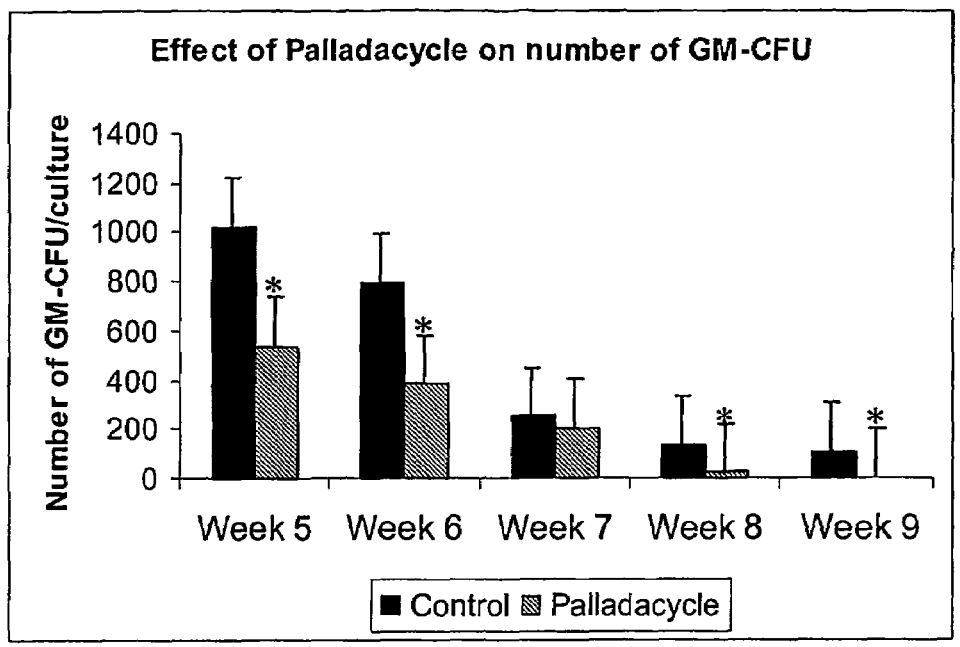

FIG. 8 presents the number of colonies of hematopoietic precursor cells for granulocytes/macrophages (CFU-GM) obtained in the supernatant of long duration cultures of bone marrow cells from normal animals treated with 1 mg/kg of cyclopalladated compounds [Pd($C^2$,N-(S-dmpa)(dppf)Cl]. Non-adhering cells were removed weekly and the number of CFU-GM was quantified (P<0.05 ANOVA, Tukey).

Figure 9:
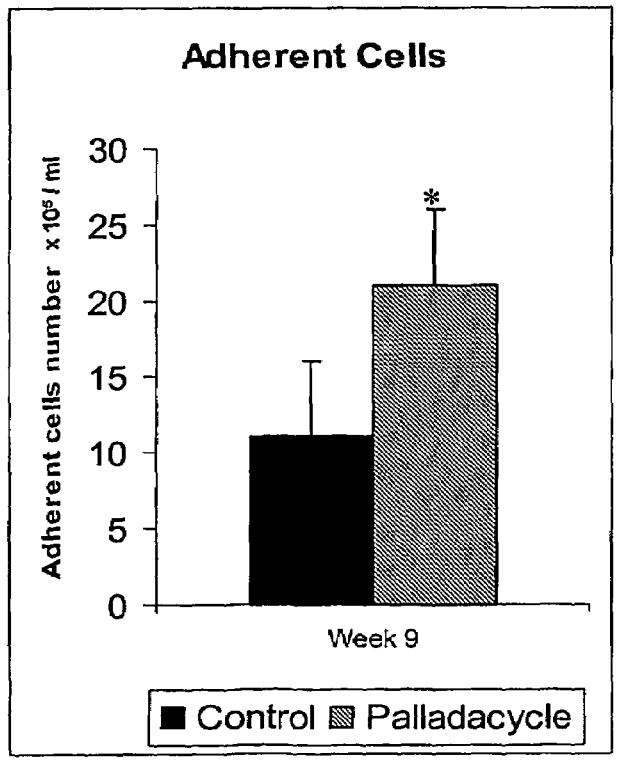

FIG. 9 presents the number of adhering cells in the long duration cultures of bone marrow cells from normal animals treated weekly with 1 mg/kg of the cyclopalladated compound [Pd($C^2$,N-(S-dmpa)(dppf)Cl]. Adhering cells were removed by the end of the culture ($9^{th}$ week) (P<0.05-Wilcoxon).

Figure 10:
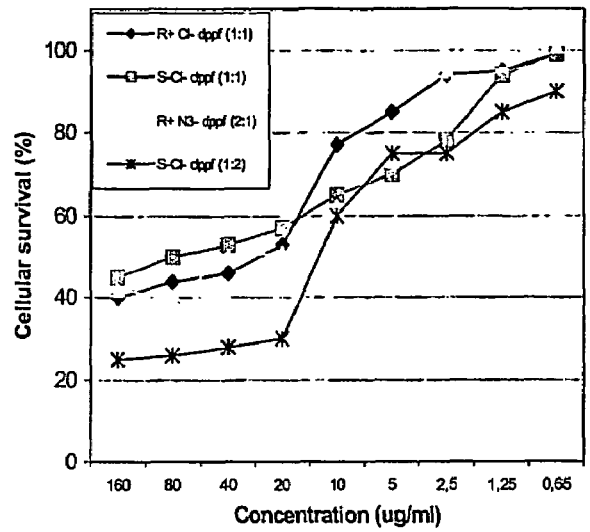

FIG. 10 presents the percentual cell life extension for HL60 cells incubated for 72 hours with various cyclopalladated compounds.

Figure 11:
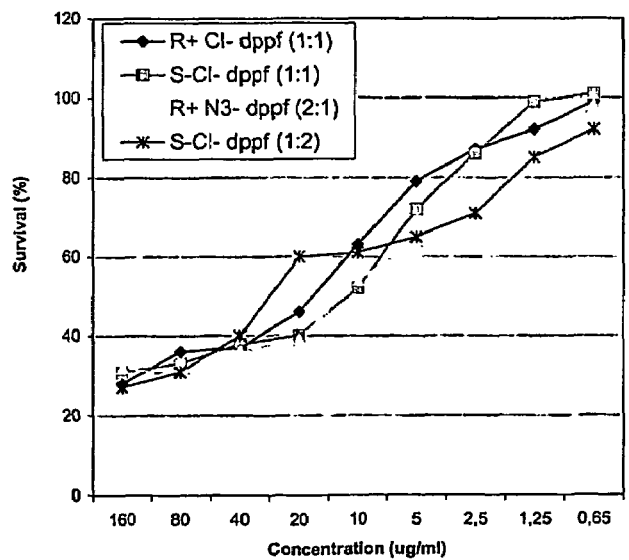

FIG. 11 presents the percentual cell life extension for K-562 cells incubated for 72 hours with various cyclopalladated compounds.

Figure 12:

FIG. 12 presents the morphological aspect of a HL60 cell incubated with the cyclopalladated compound [Pd($C^2$,N-(S-dmpa)(dppf)Cl] for 72 hours. It is possible to clearly observe the aspects of an apoptosis cell, such as nuclear fragmentation with the formation of picnotic nuclei (color: Harry's hematoxyline 400× magnification).

Figure 13:
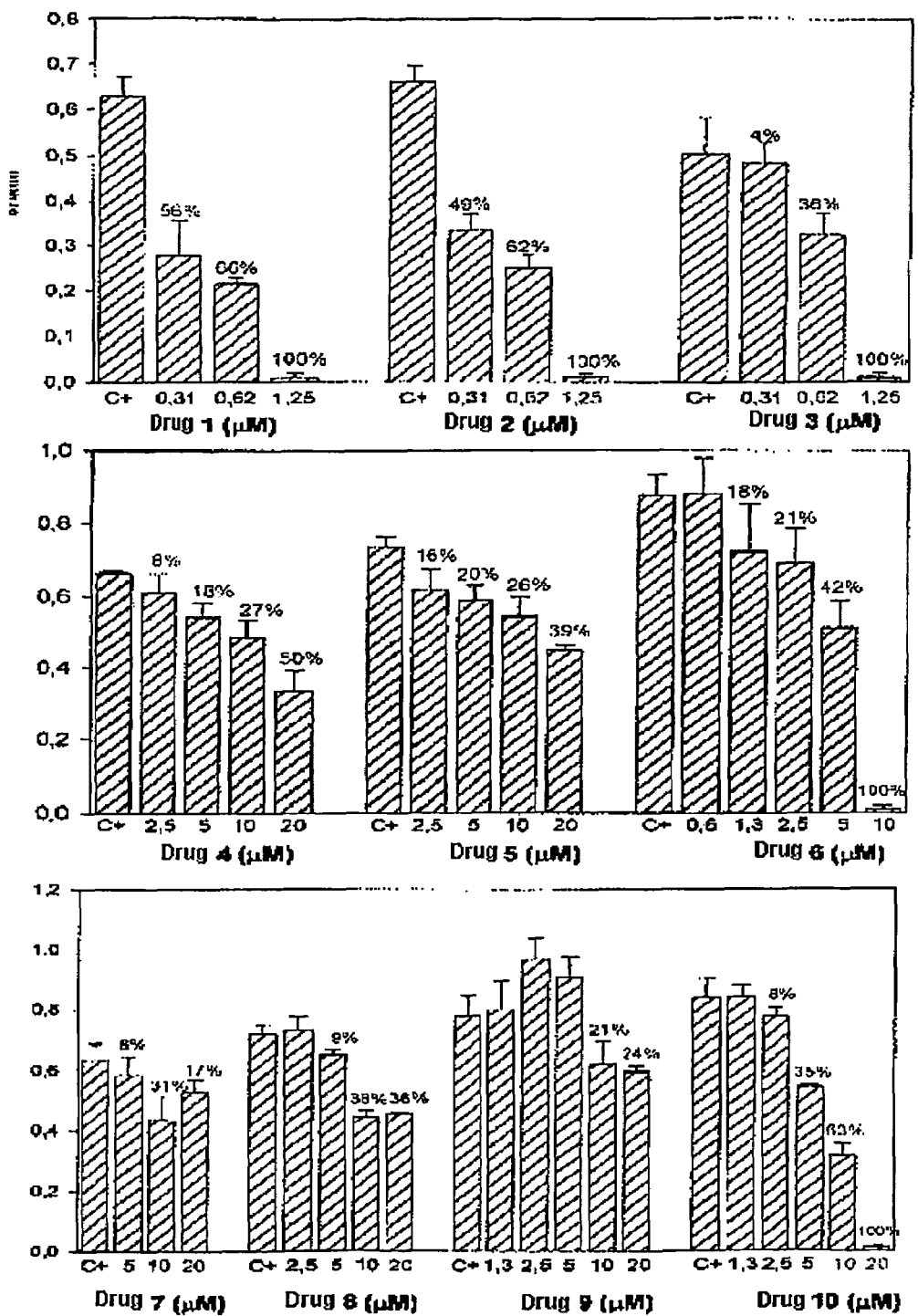

FIG. 13 presents the cytotoxic effect of the cyclopalladated compounds.

Figure 14:
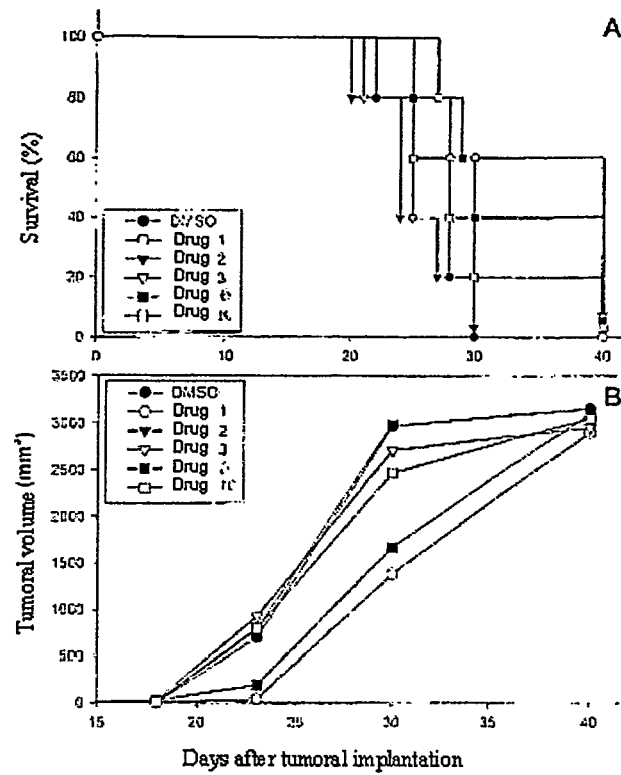

FIG. 14 presents the in vivo antitumor activity of the cyclopalladated compounds at 10 μM.

Figure 15:
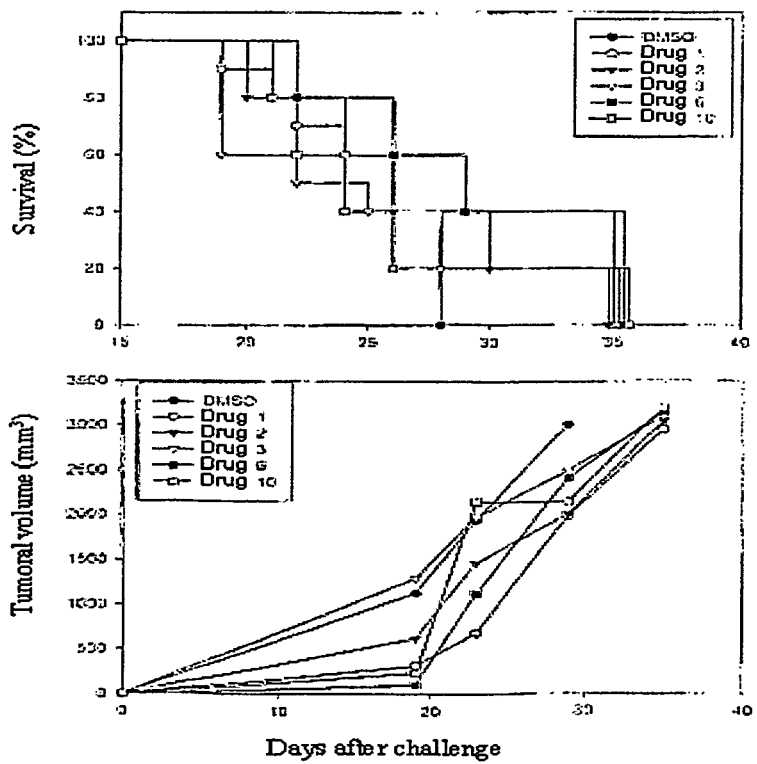

FIG. 15 presents the in vivo antitumor activity of the cyclopalladated compounds at 30 μM.

Figure 16:
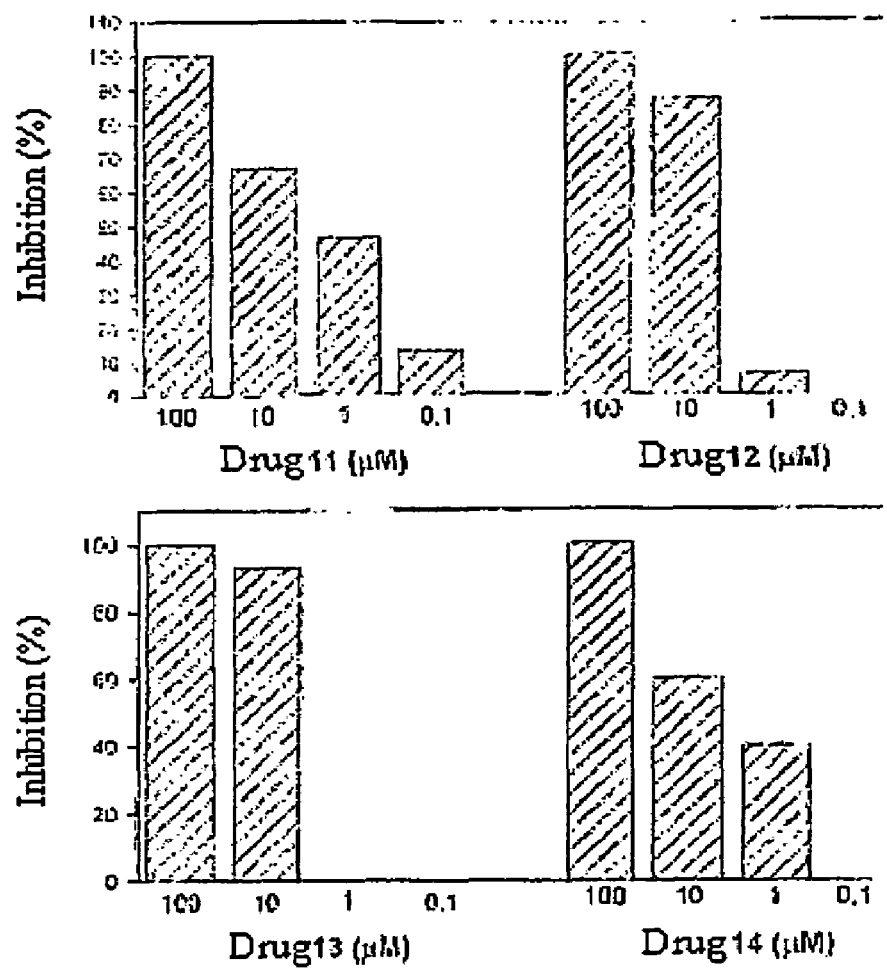

FIG. 16 presents the in vivo antitumor activity of compounds analogue to drug 1, now containing functionalized alkenes derived from functionalized alkynes as cyclometalling agent.

DETAILED DESCRIPTION OF THE PREFERRED EMBODIMENTS

Inhibition Effect Over Cysteine-Proteases

Cathepsin B

Cysteine-proteases constitute a family of enzymes having a thiol group (—SH) in the active site. They are able to cleave amide linkages by synergical interaction between a specific cysteine and a histidine in the active site by means of a known route (U.S. Pat. No. 5,880,149). These proteins are found in bacteriae, virus, eukariote microorganisms, plants and animals having four or more super families. The inhibition of Cathepsin B enzyme by the cyclopalladated compounds of the invention has been initially pointed out as the main cause of antitumor activity shown by these compounds. However, the activity of the compounds of the invention is not limited to this cysteine-protease and their use as pharmaceuticals should not be restricted to the combat against cancer.

Cyclopalladated compounds as described herein are active inhibitors for cysteine-proteases: Cathepsins B, H, J, L, N, S, T and C (dipeptidyl-peptidase-l), Interleukine Converter Enzyme (ICE), neutral proteases activated by calcium, Calpaine I and II, viral cysteine-proteases, such as cardiovirus endopeptidase, adenovirus endopeptidase and aphthovirus endopeptidase, and essential proteases for the life cycle of parasites such as proteases from *Plasmodium, Entamoebas, Onchoceras, Leishmanias, Haemonchus, Dictyostelium, Therilerium, Schistosoma* and *Tripanosoma* species (*T. cruzi*, this enzyme is also known as cruzain or cruzipain). A full list of cysteine-proteases which can be inhibited by these compounds is given by Rawlings et al (*J. Biochem.* 290: 205-218, 1993) and by Sajid M. et al (*Molecular and Biochem. Parasitology*, 120: (1) 1-21, 2002).

The use of cyclopalladated compounds as pharmaceuticals involves therefore a wide spectrum. Particularly its actuation as inhibitors for Cathepsins B, L, S, Cruzaine and Interleukine-1β Converter Enzyme, which are lysosomal proteases related to numerous disease processes caused by tissue degradation, a group comprising arthritis, muscle distrophy, tumor invasion, glomeronephritis, bone infections by parasites, periodontal diseases and tumor metastasis, among others.

Schotte et al, in his work for JBC (Vol. 276, n° 24, Issue of June 15, pp. 21153-21157, 2001), proves that Cathepsin B inhibitors prevent the production of Interleukine-1α, Interleukine-1β and tumor necrosis factor at transcriptional level, which may also be involved in the inhibition of transactivation potential of the nuclear factor $_kB$ (NF-$_kB$), resulting from gene expression. Cyclopalladated compounds therefore presenting inhibiting activity over Cathepsin B and over NF-$_kB$ constitute active pharmaceuticals for a large number of inflammatory diseases, such as bronchitis, arthritis rheumatoid, osteoporosis, acute pancreatitis and cancer progressions.

Inhibition Effect Over Serine Peptidases

Prolyl-Oligopeptidase

Prolyl-oligopeptidase constitutes a family of enzymes pertaining to the group of serine peptidases, which cannot hydrolise peptides with more than thirty residues. This group comprises dipeptidyl-peptidase IV, acylaminacyl-peptidase and oligopeptidase B, besides the prototype prolyl-oligopeptidase. A recent determination of the crystalline structure of prolyl-oligopeptidase (80 kDa) shows that the enzyme has a peptidase dominion with a folded alpha/beta hydrolase and its catalytic triad is constituted by a central tunnel having an uncommon beta-folded structure with seven blades, a dominion operating as a filter for large peptides. The inhibition of enzymes of this family is an important source of development of new drugs, since prolyl-oligopeptidases are involved in a large number of disturbances, such as amnesia, control of depression and blood pressure, also acting as important Chaperones for the transport of proteins through membranes of the endoplasmatic reticulum and mitocondriae (Sharova, E. I.; *Russian Journal of Plant Physiology*, 49 (2), 255, 2002).

Dipeptidyl-peptidase IV is involved in diabetes and oligopeptidase-B in trypanosomiasis—Polgar L., *Cellular and Molecular Life Sciences*, 59 (2), 349-62, 2002 and Folop, V. et al, *Cell*, 94 (2), 161-70, 1998. Furthermore, Maes, M. et al in *Psychoneuroendocrinology*, 26 (1), 17-26, 2001, prove the involvement of that enzyme in food disorders, bullimia nervosa and anorexia. The activity of prolyl-endopeptidase (PEP) and dipeptidyl-peptidase IV (DPP IV) in alcoholism was also proven, for the production of cytokines and cytokine receptors, such as interleukine-6 (IL-6), tumor necrosis factor alpha (TNF-alpha), interferon-gamma (INFN-gamma), IL-1 antagonist receptor (IL-1RA), IL-10 and growth stimultating factor for granulocyte-macrophage colonies (GM-CSF), and the reduction in the concentration of PEP and DPP IV increases the production of these factors (Maes, M. et al, *Alcohol*, 17 (1), 1-6, 1999). The high activity of these enzymes in the human organism is also related to psychological stress, according to Maes, M. and contributors in *Psychoneuroendocrinology*, 23 (5), 485-495, 1998.

DPP IV, also known as CD26; EC 3.4.14.5, is a glucoprotein receptor with multiple features, including cell adherence, cell transporter through the extracellular matrix and potential co-stimulator during the activation of T cells. Since it is an exopeptidase, it becomes a regulatory key for the metabolism of hormonal peptides. Selective inhibitors of that enzyme have application, among others, for the treatment of diabetes type II, in which that enzyme takes part of complex regulation cycles as described by Hildebrandt and contributors in *Clinical Science*, 99 (2), 93-104, 2000.

A review job shows the properties of DPP IV and the therapeutical potentials of its inhibitors (Augustyns, K.; Bal, G.; Thonus, G.; Belyaev, A. et al, *Current Medicinal Chemistry*, 6 (4), 311-327, 1999), evidencing its feature as antigen for leucocyte CD26 and its action over new substrates glucagon chemokines. The work also discusses the therapeutical potentials of its inhibitors for the combat against infections caused by the HIV virus (AIDS) and their co-relations to the immunological system.

Joyeau and contributors have proven, on the other hand, that the specific prolyl-oligopeptidase Tc80 is essential for the metabolism of *Tripanosoma cruzi*, with its inhibitors being potential pharmaceuticals against Chagas disease (*European Journal of Medicinal Chemistry*, 35 (2), 257-266, 2000).

Oligopeptidase B is a member of the new family of serine peptidases as found in Gram-negative bacteriae and Trypanosomes (Juhasz, T.; Szeltner, Z.; Renner, V.; Polgar, L., *Biochemistry*, 4 (12), 4096-4106, 2002). *Tripanosoma brucei* contains serine-oligopeptidase (OP-Tb) released by the host in blood circulation during the infection of *Tripanosoma africana* (Morty, R. E.; Lonsdale-Eccles, J. D.; Morehead, J. et al, *Journal of Biological Chemistry*, 274 (37), 26149-156, 1999).

Neutral endopeptidases are also responsible for the regulatory properties of Angiotensin II (Maric, C.; Walther, T., *FASEB JOURNAL*, 16 (4), A93, Part 1, 2002), with the involvement of that class with the properties described for ACE and also its relation to immunemodulation becoming clear (Inguimbert, N. et al; *Journal of Medicinal Chemistry*, 45 (7), 1477, 2002).

Cathepsin D

Cathepsin D is an acidic endopeptidase, serving as a factor for the prognostic of breast cancer (Kraimps, J. L., Metaye, T., Millet, C., Margerit, D., Ingrand, P., Goujon, J. M., Levillain, P., Babin, P., Begon, F., Barbier, J., *Surgery* 1995 Dec., 118 (6): 1036-40), being also expressed under high concentration in marrow carcinomas and thyroid tumors (Holm, R., Hoie, J., Kaalhus, O., Nesland, J. M., *Virchows Arch* 1995; 427 (3): 289-94). The activity of cathepsin D is respectively higher in cancer cells, adenomas and serious diseases of the thyroid gland than in normal cells, being located in both tumor and normal cells (Metaye, T., Kraimps, J. L., Goujon, J. M., Fernandez, B., Quellard, N., Ingrand, P., Barbier, J., Begon, F., *J. Clin. Endocrinol. Metab.* 1997 October; 82 (10): 3383-8). In cutaneous carcinomas (melanoma and nerves), the activities of Cathepsin B and L are high. Cathepsin D is only expressed under high levels in melanoma. The activity of Cathepsin H is inversely related to the invasive potential of the damage (Frohlich, E., Schlagenhauff, B., Mohrle, M., Weber, E., Klessen, C., Rassner, G., *Cancer*, 2001 Mar. 1; 91 (5): 972-82). Cathepsin D, nm23, EGFR and LR (immunohistochemically detected) are potential markers for the distance of metastatic spreading of breast cancer with negative nodule, with the combination of the three first ones being a more promising approach (Niu, Y., Fu, X., Lv, A., Fan, Y., Wang, Y., *Int. J. Cancer*, 2002 Apr. 10; 98 (5): 754-60). Imunohistochemical analysis shows that the expression of Cathepsin D by cancer cells is linked to the depth of the gastric and bowel tumor invasion (Ikeguchi, M., Fukuda, K., Oka, S., Yamaguchi, K., Hisamitsu, K., Tsujitani, S., Sakatani, T., Ueda, T., Kaibara, N., *Oncology* 2001; 61 (1): 71-8). The expression of Cathepsin D is linked to the expression of protein p53 in gullet cancer cells according to imunohistochemical analysis. Cathepsin D was not detected in sound gullet cells. High expression of Cathepsin D is significantly linked to the invasive growth of the tumor (Ikeguchi, M., Sakatani, T., Ueta, T., Fukuda, K., Oka, S., Hisamitsu, K., Yamaguchi, K., Tsujitani, S., Kaibara, N., *J. Clin. Pathol.* 2002 February; 55 (2): 121-6). Assays with rats show that Cathepsin D is directly linked to the tumor metastasis process through the transference of the expression vector of human Cathepsin D in breast cancer. Inhibitors of that enzyme, in which the cyclopalladated compounds at issue are included, directly influence the reduction or inhibition of tumor metastasis (Marcel Garcia, Nadine Platet, Emmanuelle Liaudet, Valérie Laurent, Danielle Derocq, Jean-Paul Brouillet, Henri Rochefort, *Stem Cells* 1996; 14: 642-650).

Palladium compounds of the invention are efficient inhibitors for Cathepsin D. They have also been shown as efficient inhibitors of thyroid tumors under doses of about 1 to about 10 μg. Three lines of cells from these tumors were studied: WRO, NPA, ARO, showing that the compounds described herein can be used for the development of an efficient pharmaceutical against a kind of tumor for which there is practically no treatment by a chemotherapeutical. This fact added to the immunomodulating action of the cyclopalladated compounds, inhibiting young bone marrow cells from entering cell division (stage S) make these promising pharmaceutical compounds become joint treatments for thyroid tumors, involving radio therapy and inhibiting undesirable side effects such as e.g. leukemia.

It is proven that the inhibition of lysosomal protease with enzyme inhibitors generates the death of neuroblastoma cells (Castino, R., Pace, D., Demoz, M., Gargiulo, M., Ariatta, C., Raiteri, E., Isidoro, C., *Int. J. Cancer* 2002 Feb. 20; 97 (6): 775-9). Under this aspect, cyclopalladated compounds presented herein represent an option for the treatment of this kind of cancer, mainly in children, in which it is very aggressive, without the problems consequent from the use of known compounds.

Inhibition Effect Over Metallo-Proteases

Angiotensin Converting Enzyme (ACE)

The angiotensin converting enzyme is a part of the group of metallo-proteases, containing Zinc in one of its sites, and is related to the conversion of Angiotensin I into Angiotensin II. The enzyme has two dominions, designated dominion C and dominion N, i.e. it has two active centers. Angiotensin II induces the proliferation of progenitor cells from the Hematopoietic System (HPC), while Angiotensin I inhibits that proliferation. On the other hand, the peptide Acetyl-N-Ser-Asp-Lys-Pro (AcSDKP), which is also a substrate for the ECA enzyme, is a regulator of the proliferation of parent cells from the Hematopoietic System.

We can find in the literature numerous reports on the influence and route for these substrates (Angiotensin I, Angiotensin II and the peptide AcSDKP) in the modulation of the immunological system, such as those mentioned below:

Chisi et al (*Inhibitory Action of the Peptide AcSDKP . . . , Stem Cells* 1997; 15: 455-460) describe the use of the combination of AcSDKP with appropriate ACE inhibitors to regulate the proliferation of hematopoietic cells in vitro. Significant inhibition of the young cell cycle by the action of the peptide AcDSKP in the presence of captopryl, an efficient ACE inhibitor, is noted, with effect on the active site N of the enzyme.

In another article, Chisi (*Captopryl inhibits the proliferation of hematopoietic stem and progenitor cells . . . , Stem Cells* 1999; 17: 339-344) also discloses that drugs used to treat hypertension as ACE inhibitors may cause pancitopeny, but the reason for that is still unknown. Studies showed that captopryl did not present toxicity for bone marrow cells, but it reduces the proportion of S-stage macrophages; these results indicate that captopryl causes mielosuppression.

Azizi et al (*Angiotensin l-converting Enzyme . . . , Clin. Exp. Pharmacol. Physiol.* 2001 December; 28 (12): 1066-9) describe that AcSDKP is hydrolysed by ACE in vitro and is a preferential substrate for the N-terminal of the active site of that enzyme, but is also a natural peptide hydrolised by the N terminal of the active site of ACE in vivo. ACE can then regulate hematopoiesis by the permanent degradation of that natural inhibitor circulating within S-stage cells. The phosphinic peptide RXP407 (a selective inhibitor for the N dominion of ACE in vitro) does not interfere with blood pressure regulation.

Aidoudi and contributors (*The Tetrapeptide AcSDKP Reduces . . . , Int. J. Hematol.* 1998 August; 68 (2): 145-55) tested AcSDKP protection in progenitor cells for CFU-MK and CFU-GM in mice treated with a low dosage of cytosine arabinoside (Ara-C), both in vitro and in vivo assays. It was shown that the administration of AcSDKP before starting treatment with Ara-C results in a significant increase of CFU-GM, CFU-MK and maturation of the number of MK cells between six and eight days after the first injection of Ara-C. Results showed protecting effect of AcSDKP for progenitor cells during the treatment with Ara-C.

Rousseau-Plasse (*Lisinopryl, an Angiotensin l-converting Enzyme Inhibitor . . . , Exp. Hematol.* 1998 October; 26 (11): 1074-9) reports that the oral administration of ACE inhibitors to humans increased the concentration of AcSDKP in plasma. The effect of lisinopryl in the proliferative state of hematopoietic cells of mice in the S stage caused by radiation was studied in vivo. The administration of lisinopryl one hour after radiation inhibited 100% murine plasma activity for ACE due to the increase in the endogenous plasma level of AcSDKP.

Li et al (*Production and Consumption of the Tetrapeptide AcSDKP . . . , Exp. Hematol.* 1997 February; 25 (2): 140-6) analysed the role of the human cell microenvironment in the metabolism of AcSDKP, using long-term marrow cell culture (LTMC). The results obtained showed that: macrophages synthesize and release AcSDKP in the supernatant; stroma cells degrade the peptide by ACE; and components of the extracellular matrix and LTMC serve as a reservatory for the peptide.

When evaluating the effects of the compounds of the invention in the long-term liquid culture system (prolonged exposure in vitro), allowing to evaluate the effects of the compound over the formation of marrow stroma (tissue formed by fibreblasts, lipid signaling cells and endothelial cells, among others), which is responsible for sustaining young bone marrow cells (stem cells), it was found that the prolonged exposure to those compounds, particularly those containing the coordinated ligand 1,1'-bis-diphenylphosphine-ferrocene, as represented in the generic structures A and B as described, significantly increase the adhering cells to the marrow stroma in comparison to the control. On the other hand, a reduction in the number of non-adhering cells in the supernatant of liquid cultures and a reduction in the number of cell colonies (CFU-GM) obtained from the supernatant of these cultures was observed. This response standard was observed with drugs inhibiting the angiotensin converting enzyme (ACE), such as captopryl. The above-mentioned studies show that this drug inhibits ACE, increasing the concentration of the tetrapeptide AcSDKP (ACE substrate), which is produced by marrow stroma cells and acts inhibiting pluripotent cells from the bone marrow to enter the cell cycle. This fact is particularly interesting, since chemotherapeutical drugs act particularly in the S stage of the cell cycle (DNA synthesis), reaching not only malignant cells, but also those from quickly renewed tissues, such as the bone marrow. The temporary interruption of the cell cycle as produced by the cyclopalladated compound is linked to higher protection to bone marrow cells against myelotoxic effects of conventional chemotherapy.

The compounds of the invention are immunomodulators, as the reversible reduction of bone marrow cell proliferation (granulocytes and macrophages) is linked to lower phagocytic activity and reduction in the release of interleukine 1 by macrophages, with consequent reduction in lymphocyte stimulation which, on the other hand, are also involved in the progression of autoimmune diseases. Therefore, compounds as described herein are useful as immunosuppressants.

Route

The route of action of the compounds of the invention occurs in a mainly reversible way, thus resulting in low cytotoxicity and reduction of undesirable side effects.

Without being bound by theoretical aspects, the enzymatic inhibition route is presented e.g. as ionic cyclopalladated complexes containing biidentated dppf ligand of the type [Pd($C^2$,N-dmpa)(dppf)]X. Firstly, a coordination bond is broken between the phosphorous atom of the biphosphinic linker and the ion Pd(II) with simultaneous coordination of a molecule of the solvent DMSO, thus producing the complex [Pd($C^2$,N-dmpa)(dppf)(DMSO)] X. The same complexes containing DMSO (or another coordinating solvent such as dimethylformamide, piridine, THF and others) can be formed by cyclopalladated complexes of the molecular type [Pd($C^2$,N-dmpa)(dppf)X], with the migration of a X$^-$ ion in solution to outside the metal coordination sphere. From the cyclopalladated complexes presenting bridged dpf linkers of the type [$Pd_2$($C^2$,N-dmpa)$_2$($\mu$-dppf)$_2$$X_2$], the complexes [Pd($C^2$,N-dmpa)(dppf) (DMSO)]X are probably produced by partial decomposition of the complex in a DMSO/water solution due to their lack of stability in DMSO solutions. This fact is clearer when Pd(0) is formed after a few minutes of dissolution of the complexes in a DMSO solution. The solution of the complex [$Pd_2$($C^2$,N-dmpa)$_2$($\mu$-dppf)$_2$($N_3$)$_2$] in nitromethane shows an increase in molar conductivity from 9.3 S.cm$^2$ to 60 S.cm$^2$ at 25° C., by the addition of a few drops of DMSO.

In a next stage, the complex [Pd($C^2$,N-dmpa)(dppf) (DMSO)]X, by rupture of the coordinated linkage N—Pd and coordinating the new DMSO molecule, produces probably the complex [Pd($C^2$-dmpa)(dppf)(DMSO)$_2$]X. This last organometallic molecule generated in solution is the most probable inhibitor of the enzymatic action.

Considering the fact that the free dppf ligand and no other complex formed by other classes of biphosphinic ligands were able to inhibit enzymatic activity, we conclude that the inhibition phenomenon is highly depending on the dppf biphosphinic ligand, as well as the chemical structure of the complex of palladium. In this fashion, we believe that the organometallic inhibitor produced in solution, i.e. the complex [Pd($C^2$,N-dmpa)(dppf)(DMSO)]X, reaches dynamic balance with the tetrahedric intermediary complex produced by association between the couple of thiolate-imidazol ions with the substrate. This interaction occurs with the participation of two metal centers existing in the complex (Pd, Fe). In this model, the high-density acyl group of negative charges interacts with the ion Pd(II) by simultaneous displacement of a DMSO molecule, coordinating to a highly activated sulphur atom from the cysteine group, which on the other hand interacts with the iron atom from the dppf ligand. The balance of the species in solution originates a reversible inhibition route.

The invention refers to cyclopalladated compounds comprising bis-diphenylphosphine-ferrocene linkers and other analogue linkages containing donor atoms from the same phosphorous group as protein inhibitor actives, particularly enzymes. Acting over these enzymes and taking part of insertions with DNA molecules, these compounds modulate the immunological system.

In a particular embodiment, enzymes which activity is inhibited by the compounds of the invention pertain to the families of serine peptidases, cysteine-proteases, metallo-proteases and endopeptidases.

In a more particular embodiment of the invention, cysteine-proteases inhibited by the compounds herein disclosed are Cathepsins B, H, J, L, N, S, T and C (dipeptidyl-peptidase-1), Interleukine Converter Enzyme (ICE), neutral proteases activated by calcium, Calpaine I and II, viral cysteine-proteases, such as cardiovirus endopeptidase, adenovirus endopeptidase and aphthovirus endopeptidase, and essential proteases for the life cycle of parasites such as proteases from *Plasmodium, Entamoebas, Onchoceras, Leishmanias, Haemonchus, Dictyostelium, Therilerium, Schistosoma* and *Tripanosoma* species (*T. cruzi*, this enzyme is also known as cruzaine or cruzipain).

In an even more particular embodiment, cysteine-proteases inhibited by the compounds of the invention are Cathepsine B, Cruzipain and Interleukine-1β Converter Enzyme.

In a more particular embodiment of the invention, serine peptidases inhibited by the compounds disclosed herein are dipeptidyl-peptidase IV, acylaminacyl-peptidase, oligopeptidase B and prolyl-oligopeptidase.

In a more particular embodiment of the invention, the metallo-protease inhibited by the compounds disclosed herein is the Angiotensin Converting Enzyme (ACE). The four classes of matrix metallo-proteases (MMPs), i.e. Collagenases, Stromelisins, membrane-type Metallo-protease and Genatinases may be inhibited by these compounds. Therefore, the presented compounds can then be efficient for the treatment of inflammatory diseases of the Central Nervous System causing Mieline degradation, including Multiple Sclerosis and autoimmune Encephalomielitis (Cuzner, M. L., Opdenakker, G.; *Journal of Neuroimmunology;* 94, 1-14, 1999).

In another particular embodiment, endopeptidase inhibited by the compounds disclosed herein is Cathepsin D. Encephalinase or Endopeptidase 24.11 also suffer inhibition by the described compounds. Therefore, they have application in heart diseases involving degradation of the atrial natriuretic factor (ANF). Varin, J., Duboc, D., Weber, S., Fouchard, J., Schwartz, J. C., Muffatjoly, M., Guerin, F.; *Archives Des Maladies Du Coeur Et Des Vaisseaux;* 84, 1465-1471, 1991.

In a particular embodiment, diseases which may be treated with the compounds of the invention comprise: diseases caused by tissue degradation such as arthritis, muscle distrophy, tumor invasion, glomerulonephrithis, bone infections by parasites, parasitomies, periodontal diseases and tumor metastasis, among others; heart diseases involving the degradation of atrial natriuretic factor; inflammatory diseases, such as e.g. bronchitis, arthritis rheumatoid, osteoporosis, acute pancreatitis and cancer progressions; disorders such as amnesia, control of depression and blood pressure; diabetes, tripanossomies, Chagas disease, food disorders, bullimia nervosa and anorexia; alcoholism, diseases related to the production of cytokines and cytokine receptors, such as interleukine-6 (IL-6), tumor necrosis factor alpha (TNF-alpha), interferon-gamma (INFN-gamma), IL-1 antatonist receptor (IL-1 RA), IL-10 and growth stimulation factor for granulocyte-macrophage colonies (GM-CSF), psychological stress, combat against infections caused by HIV virus (AIDS); inflammatory diseases of the Central Nervous System causing mieline degradation, including Multiple Sclerosis and autoimmune Encephalomielitis. Besides being involved in ACE inhibition which, on the other hand, is related to the modulation of the immunological system, regulation of the proliferation of progenitor cells from the Hematopoietic System and significant inhibition of the young cell cycle; hypertension with no mielosuppression. The action of the cyclopalladated compounds disclosed by the invention also causes the inhibition of invasive growth of tumors, such as breast, marrow, adenoma, thyroid, melanoma, gastric, bowel, gullet cancer and thyroid tumors. In the case of thyroid cancer, when employed together with radiotherapy, they inhibit undesirable side effects, such as e.g. leukemia. They can also be used for the combat against neuroblastomas. Cyclopalladated compounds as described present antiangiogenic and antimetastatic properties, concerning the treatment of malignant tumors.

By acting over these enzymes and taking part of insertions with DNA molecules, these compounds modulate the immunological system, thus constituting not only efficient antitumor agents, mainly in the combat against malignant tumors, but also as active substances in other diseases linked to tissue degradation, diseases caused by inflammatory processes and/or originated in virus, bacteria or parasite, autoimmune diseases, diabetes, amnesia, nervous and food disorders, stress, alcoholism and hypertension, among others. Besides being highly efficient as immunomodulators and immunosupressants, the drugs of the invention can act under low concentrations, with low cytotoxicity, presenting antiangiogenic and antimetastatic properties in the specific case of cancer treatment.

Synthesis

The palladium complexes of the invention containing the azida ($N_3^-$) group were synthesized for this group to constitute a "spectroscopical probe" in the infrared region, for more precise structural characterization over the ionic or molecular character of the complexes, as well as their mono or binuclear nature. This group has normal vibration modes in IV in the regions of 2040-2060 $cm^{-1}$ (asymmetrical stretching) and 1400-1500 $cm^{-1}$ (symmetrical stretching), facilitating said attributions. Although these complexes also presented biological effects as antitumor and enzyme inhibitors, they do not constitute the most appropriate compounds for use as pharmaceuticals, since they present undesirable cytotoxic and side effects, affecting the cell breathing cycle. For all synthesized complexes containing the azida group, analogues were obtained with chloride ($Cl^-$) ion, not presenting said secondary effects and constituting equally active drugs.

The synthesis of the compounds was made under room temperature by using reagents with high purity grade from commercial suppliers with no additional purification. Elementary analysis was made by IQ-USP-SP-Brazil Analytical Center. FT-IR spectra were obtained in a spectrophotometer Perkin-Elmer *Spectrum-One* in the range of 4000-400 cm$^{-1}$ with tablet-shaped KBr samples. $^1$H and $^{31}$P{$^1$H} NMR spectra were obtained in a multinuclear spectrometer Bruker Avance DPX-300 at 300 and 81 MHz, respectively. Proton NMR data were registered in ppm, by using TMS at 0.00 ppm as a reference. 31P{$^1$H} chemical displacements were measured as related to H$_3$PO$_4$. All NMR measurements were obtained in the solvent CDCl$_3$. Molar conductivity measurements for the complexes were made in a conductivemeter *Metrohm mod.* 712, using nitromethane as a solvent. Starting complexes are illustrated by Example 1. Particular embodiments of the invention can be verified in the preparation of starting complexes and further examples.

Preparation of Complexes with Biphosphinic Ligands

From the starting complexes described by Example 1, numerous cyclopalladated complexes were synthesized, according to particular embodiments of the invention, by reactions with 1,1'-bis-diphenylphosphine-ferrocene (dppf). The resulting product depends on the used stoechiometry and solvent. Molecular and ionic complexes were isolated having 1 or 2 metal centers and containing the biphosphinic coordination ligand in the mono or bi-toothed way for the palladium ion(II).

General Procedure

Ionic compounds presenting chelated biphosphinic ligands of the type [Pd(C$^2$,N-dmpa)(L)]X (L=bidentated ligand) were synthesized from reactions between the starting cyclopalladated complexes and biphosphinic linkers (L-L). Molar reason 2:1 between the biphosphinic linker and the respective palladium complex was used. Thus, 0.2 mmol of the dimeric cyclopalladated compound was partially dissolved in 50 ml of acetone in an Erlenmeyer. Then, 0.4 mmol of (L-L) was added to the resulting suspension. The mixture remained over constant shaking under room temperature for one hour. The solvent of the final mixture was evaporated under almost dry pressure and the resulting solid then deposited with the addition of hexane. The solid was subsequently washed with Et$_2$O and dried under vacuum.

Molecular compounds presenting biphosphinic monodentated ligand of the type [Pd(C$^2$,N-dmpa)(L)X] (L=monodentated ligand) were synthesized by a similar procedure, using dichloromethane as the solvent.

Binuclear cyclopalladated complexes presenting bridged biphosphinic linkers of the type [Pd$_2$(C$^2$,N-dmpa)$_2$(μ-L)X$_2$] (L=bridged biphosphinic linker) were obtained by using molar ratio 1:1 of the biphosphinic linker and the respective palladium complex with dichloromethane as the solvent. Said preferential embodiments of the invention are illustrated by Examples 2 to 4.

Interaction Between Compounds and Enzymes

Cathepsin B and papain were supplied by the company Calbiochem Co. and the concentration of active enzymes was determined by titulation by using the cysteine-protease inhibitor known as E-64. Cathepsin B and papain were packed at 4° C. within 50 mM in sodium acetate buffer (pH 5.0) containing 10 μM MMTS. The fluorogenic substrate amidomethylcoumaryl Z-Phe-Arg-MCA, tripsin and the irreversible papain inhibitor E-64 were supplied by Sigma.

The influence of the organometal compounds on the activity of endopeptidase cathepsin B was determined by spectrofluorimetry, using the fluorogenic substrate Z-Phe-Arg-MCA. This peptide is a good substrate for cathepsin B with k$_{cat}$/Ks=4.5 10$^5$ M$^{-1}$.s$^{-1}$ and was chosen so to locate residues Phe and Arg in P$_2$ and P$_1$, respectively. The substrate covers the main linkage sites S$_2$, S$_1$ and S'$_1$ with cysteine-proteases similar to papain (Turk, D. et al, *Revised definition of substrate binding sites of papain-like cysteine proteases, J. Biol. Chem.;* 1998, 379, 137-147).

The intensities of fluorescence signals were monitored by a thermostatic spectrofluorimetry Hitachi F-2000. Wavelength was calibrated at 380 nm for excitation and 440 nm for emission. The activation of the enzyme was made by incubation for five minutes at 37° C. in a buffer solution of 50 mM sodium phosphate (pH 6.4) containing NaCl 200 mM, EDTA 1 mM and DTT 2 mM. Measurements were taken in the same activation buffer of cathepsin B and kynetic standards were set up by taking the initial hydrolysis rate under various concentrations of the substrate in the presence or absence of different concentrations of organometal compounds. The results were analysed by non-linear regression by using the software GraFit 3.01 (Erithacus Software Ltd.).

The Kynetic model of Scheme 1 describes the effect of heparin over the hydrolysis of Z-Phe-Arg-MCA by cathepsin B:

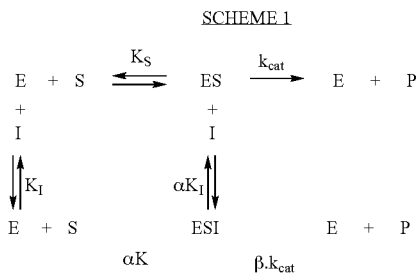

SCHEME 1

In which S represents the substrate Z-Phe-Arg-MCA; I represents the cyclometal compound; E represents cathepsin B; K$_S$ represents the dissociation constant of the substrate; K$_I$ represents the apparent dissociation constant of the organometal; α is a disturbance standard of K$_S$; and β is a disturbance standard of V$_{max}$ (k$_{cat}$), with the standards being in accordance to the equation:

$$v = \frac{V_{max} \cdot [S]}{Ks \frac{\left(1 + \frac{[I]}{K_I}\right)}{\left(1 + \frac{\beta \cdot [I]}{\alpha \cdot K_I}\right)} + [S] \frac{\left(1 + \frac{[I]}{\alpha \cdot K_I}\right)}{\left(1 + \frac{\beta \cdot [I]}{\alpha \cdot K_I}\right)}}$$

Figure 1:
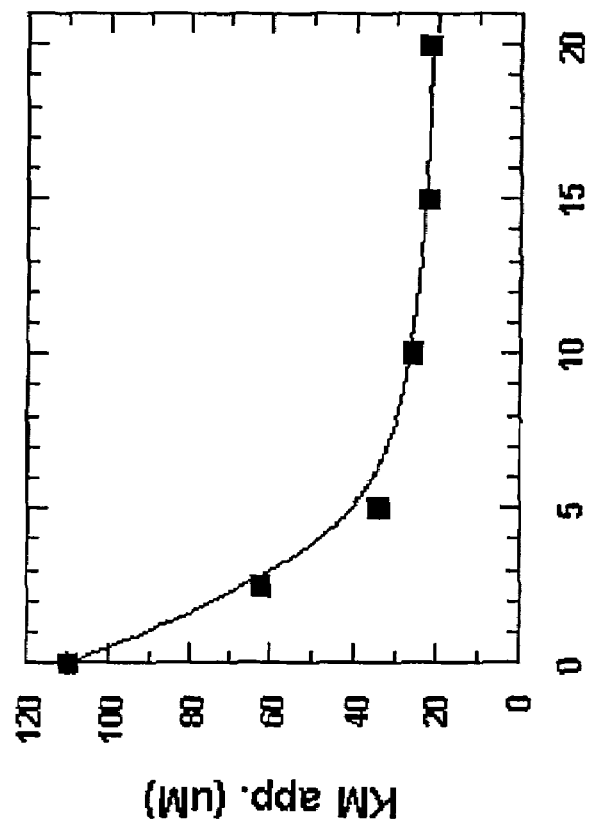
FIG. 1 presents the effect of the cyclopalladated compound over the activity of cathepsin B.
Figure 1:
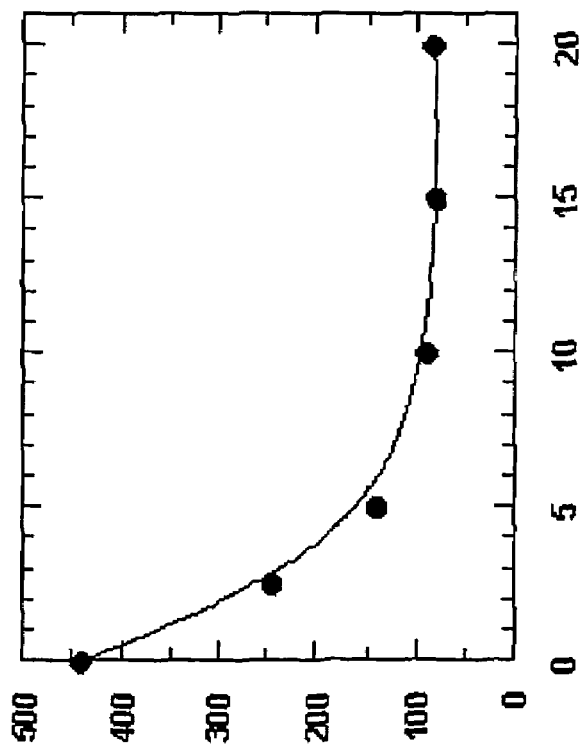

Kynetic studies were made for the cyclopalladated complex [Pd (C$^2$,N-(R+dmpa)(dppf)N$_3$]. As shown by the FIG. 1A, the presence of organometal in the kynetic test of Cathepsin B results in a reduction of the values k$_{cat}$ for the hydrolysis of Z-Phe-Arg-MCA. On the other hand, FIG. 1B shows that the compound also notedly increases the affinity of Cathepsin B by the substrate Z-Phe-Arg-MCA. The effect of organometal over the activity of endopeptidase Cathepsin B can be described by means of a mixed hyperbolic curve with inhibition standard as shown by Scheme 1. The efficiency of the substrate hydrolysis system can be changed by modifications in $K_s$ (parameter α) or $V_{max}$ (parameter β). Data were treated according to Equation 1, by using non-linear regression and the values for the constants were calculated. Results show that [Pd $(C^2,N-(R+dmpa)(dppff)]N^3$ is linked to free Cathepsin B (E) with dissociation constant $K_H$=12±1 µM and the compound is linked to the enzyme-substrate (ES) complex with dissociation constant $\alpha K_H$=2.4±0.3 µM. The complex also induced a 5.3-time increase of the affinity between Cathepsin B and the substrate Z-Phe-Arg-MCA; $K_s$ value was reduced from 110±15 to 21±2 µM in the presence of the organometal compound, α =0.19±0.02 (FIG. 1B), while the value of $k_{cat}$ in the presence of ]Pd($C_2$,N-(R+dmpa)(dppff)] $N_3$ was also reduced 5.6 times, β=0.18±0.02. The cyclopalladated compound reduced the product formation constant to 36 (β=0.18±0.02) in the same proportion increasing the affinity of Cathepsin B by the substrate Z-Phe-Arg-MCA (α=0.19±0.02), i.e., .α=β. Despite Cathepsin B having been strongly inhibited by the organometal complex (81% inhibition), its efficiency for that substrate in the presence of the organometal complex was not changed, β/α=1.1±0.1. The hydrolysis rate of the second order substrates was the same, $k_{cat}/K_s$=4.5 $10^5$ $M^{-1}s^{-1}$, in the presence or absence of [Pd $(C^2,N-(R+dmpa)(dppf)]N_3$.

Cathepsin B and other cysteine-proteases pertaining to the papain superfamily contain highly conserved folding structure (Turk, V.; Bode, W., *Lysosomal cysteine proteinases and their inhibitors cystatins. Innovations in Proteases and their Inhibitors.* Aviles, F. X. (Ed.), Walter de Gruyter & Co., Berlin, Germany, 1993). These enzymes are linked to peptide substrates and use the pair of ions thiolate-imidazolium to act in its proteolytic activity. This association between the cysteine residue and histidine grants high nucleofilicity to the active site of the cysteine (Michaud, S.; Gour, B. J., *Cathepsin B inhibitors as potential anti-metastatic agents.* Exp. Opin. Patents., 1998, 8, 645-672). The rupture of amide linkages of the substrate involves the formation of an intermediate acyl enzyme. After the formation of the non-covalent complex of Michaelis, the active site thiolate attacks the peptide linkage to form an oxianion which is stabilized in the so-called "oxianion channel" by a glutamine residue. The collapse of the tetrahedric intermediate results in the acyl enzyme and releases product. Subsequently, the hydrolysis of the acyl enzyme regenerates the catalytic ionic pair and releases the new product, i.e. carboxylic acid. Example 5 shows enzymatic inhibition assays by means of the compounds of the invention.

The results confirm the statement regarding the action of the compounds of the invention, especially reversibly in the Enzyme-Substrate complex.

Interaction Between Compounds and DNA

Insertion

Figure 2A:
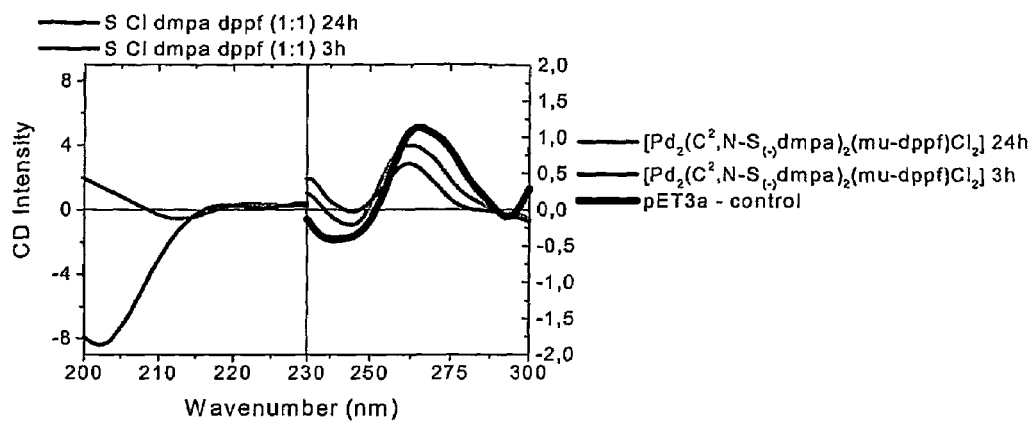
FIGS. 2A and 2B respectively present CD spectra/interaction with DNA molecules.
Figure 2B:
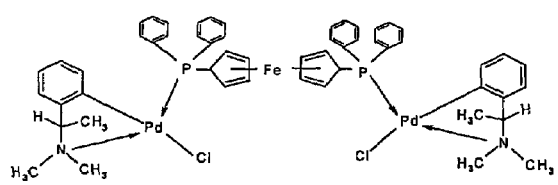

Studies by Circular Dicroism skills (FIG. 2) show structural changes caused by cyclopalladated compounds in DNA molecules, depending on time and drug concentration. This means they are involved in apoptosis and cell cycle control processes.

Antitumor Effects

Figure 3:
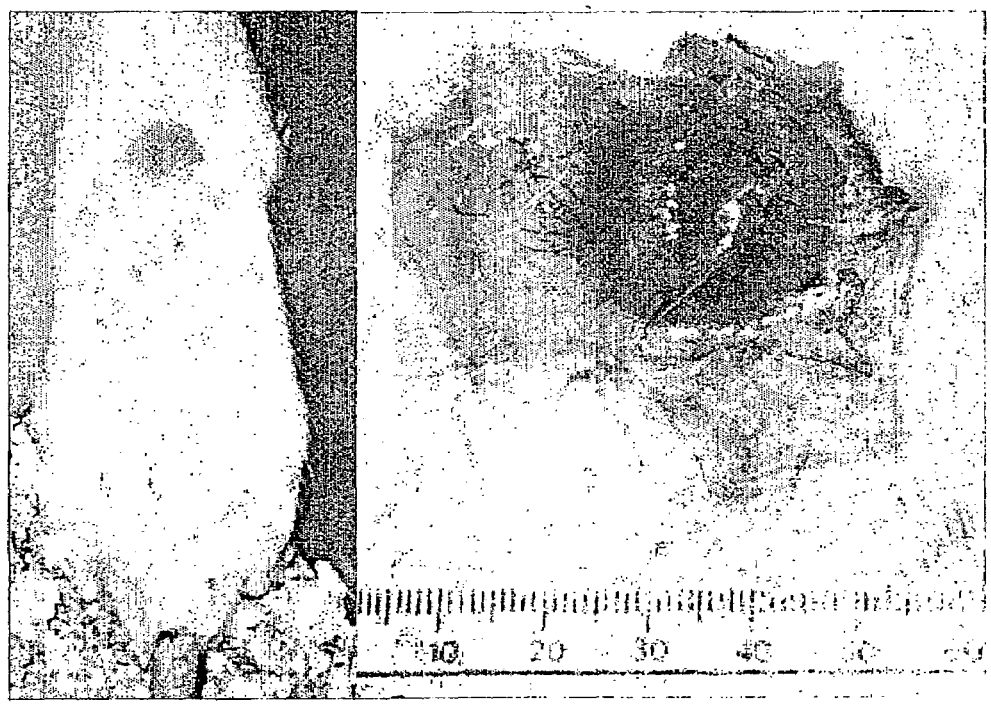
FIG. 3 presents Walker's Tumor (10 days) in a non-treated test animal.
Figure 4:
FIG. 4 presents a treated test animal (10 days) with no vestige of tumor (Walker's Tumor).
Figure 5:
FIG. 5 presents a test animal with Walker's tumor (10 days), in which the right side was not treated (12 g of tumor mass) and the left side was locally treated (2 g of tumor mass).

The compounds of the invention were tested in in vivo models, using rats as test animals and the mamary carcinoma of Walker-256, "Walker's Tumor", as a model of solid, invasive and metastatic tumor, over which the compounds showed much activity. Example 6 and FIGS. 3, 4 and 5 show the experiments and the obtained results.

We noticed that the compounds, besides inhibiting the tumor growth, manage to revert the tumor growth in 90% of the cases. For the Walker's tumor as mentioned, the compound presented in the in vivo model selective cytotoxicity for tumor cells, with no chronic signals of inflammation when the drug was applied over normal tissues. Another important action was the inhibitory effect over endothelial cell proliferation in culture, showing an important antiangiogenic action. The compounds also presented in the in vivo model large inhibitory action over Cathepsin B and over Cathepsin D, being an effective antimetastasis agent, avoiding tumor metastasis in the skeleton muscle.

The fact that no side effects were observed in none of the animal tests by any treatment must be highlighted, thus revealing high drug specificity. FIGS. 3, 4 and 5 below show some of the obtained results.

Effects on the Immunological System

Ehrlich's Ascitic Tumor (EAT)

With the purpose to observe a possible protection of treated animals with the compounds of the invention, a life extension curve was drafted, considering animals with the Ehrlich's ascitic tumor, be them treated or not.

The Life Extension Curve of Kaplan-Meier was used to analyse the possibility of survival. The comparison between both groups (holders of tumor vs. holders of tumor/treated) was made by the Log-Rank method—non-parametrical procedures (Cox-Mantel). ANOVA variation analysis was used for the analysis of various groups. In case of significant difference, the Tukey's test was applied. In cases in which the number of samples between two groups was small, the Wilcoxon's non-parametrical test was used.

Figure 6:
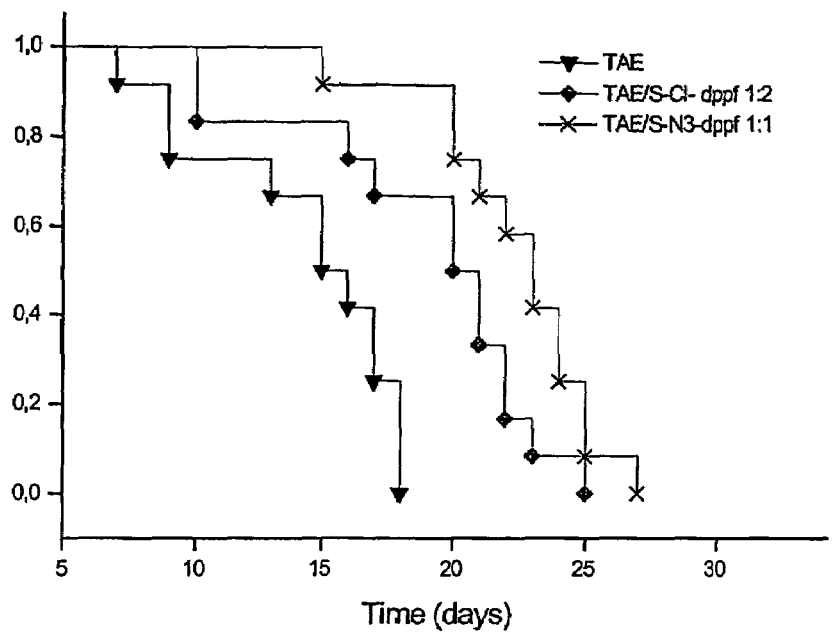
FIG. 6 presents the life extension for animals having the ascitic tumor of Ehrlich and treated (subcutaneously) with 1 mg/kg of the compounds [Pd($C^2$,N-(S-dmpa)(dppf)Cl] or [Pd ($C^2$,N-(S-dmpa)(dppf)(N$_3$)$_2$] for four consecutive days. The animals were inoculated with tumor cells ($1 \times 10^6$ cells/ml) and the treatment with the compounds being studied was started 72 hours after said procedures (p<0.05 Kaplan-Meier, Cox-Mantel).

The tests shown by Example 7 and FIG. 6 show that the treatment of animals with the compounds of the invention resulted in an increase in life extension of animals holding Ehrlich's ascitic tumor, indicating that these drugs interfere with tumor progression.

Toxicity

Clonal Culture of Hematopoietic Precursors from the Bone Marrow of Mice (CFU-C)

When the number of hematopoietic precursors for granulocytes and macrophages (CFU-GM) of the bone marrow of animals treated for four consecutive days with the cyclopalladated compound containing the ligand 1,1'-bis-diphenylphosphine-ferrocene was evaluated in 1:2 structures, as per the scheme C (generic structures), which procedure was shown by Example 8, the lack of myelotoxicity was verified under the dosage of 1 mg/kg, since there was no significant difference in the number of hematopoietic precursors for granulocytes/macrophages (CFU-GM) in treated animals in comparison to the control group, thus proving the absence of marrow toxicity under that dosage. Similar results were verified with the same dosage in the in vitro studies (incubation of normal animal cells with the compounds at issue). On the other hand, higher dosages than 5 mg/l caused reduction in the number of dose-dependent CFU-GM, indicating that the effects of that compound over bone marrow are dose-dependent.

Formation of Marrow Stroma in the Long-Lasting

Liquid Culture System

Figure 7:
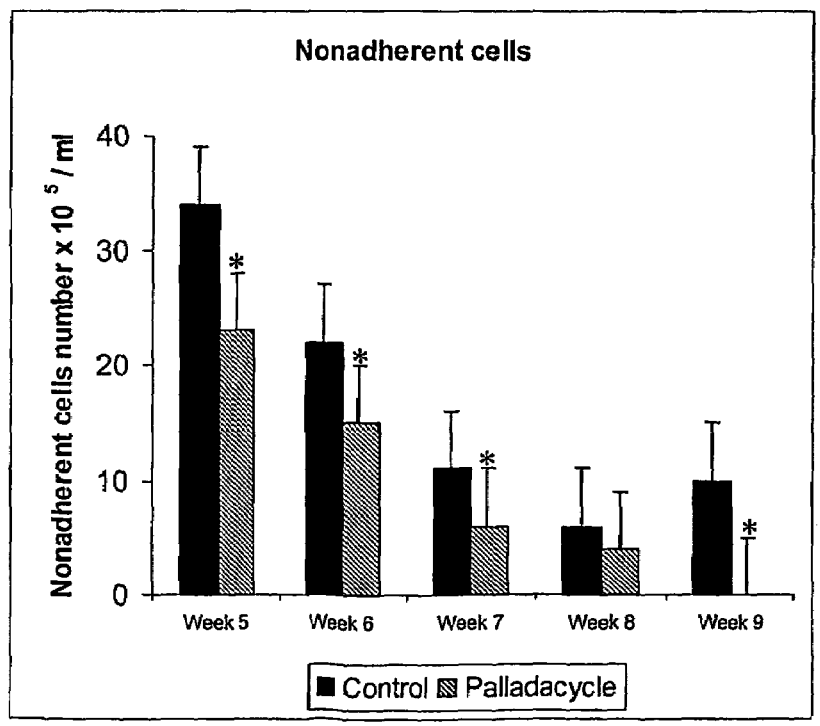
FIG. 7 presents the number of cells not adhering to the supernatant of the long duration cultures incubated with 1 mg/kg of the cyclopalladated compound [Pd($C^2$,N-(S-dmpa)(dppf)Cl]. Non-adhering cells were removed and quantified weekly (*P<0.05 ANOVA, Tukey).

When evaluating the effects of the cyclopalladated compound containing the ligand 1,1'-bis-diphenylphosphine-ferrocene in 1:2 structures, as per scheme C (generic structures) in the long-lasting liquid culture system, following the procedure illustrated by Example 9, which allows to evaluate the effects of that compound over the formation of marrow stroma, we verified that prolonged exposure of these cells to that compound reduces both the number of non-adhering cells from the supernatant of the liquid cultures (FIG. 7), and the number of cell colonies obtained from the supernatant of those cultures (FIG. 8). On the other hand, there was significant increase in the number of adhering cells from the marrow stroma in the presence of the cyclopalladated product in comparison to the control (FIG. 9). This response standard has been observed with drugs inhibiting the angiotensin converting enzyme (ECA), such as captopryl, which acts inhibiting pluripoent cells (stem cells) of the bone marrow from entering the cell cycle. Therefore, the temporary interruption of the cell cycle may be linked to higher protection to bone marrow cells against myelotoxic effects of chemotherapy.

Considering that the cyclopalladated compound containing the ligand1,1'-bis-diphenylphosphine-ferrocene in 1:2 structures as per scheme C (generic structures) is an ECA inhibitor and the results concerning the formation of marrow stroma in the long-lasting liquid culture system, such as the increase of adhering cells linked to a reduction in progenitor cell colonies CFU-GM, indicating the ability of that drug to inhibit young bone marrow cells from entering the cell cycle, even under low concentrations (1 mg/kg)

These results also show that the compounds of the invention are immunomodulators, as the reversible reduction of bone marrow cell proliferation (granulocytes and macrophages) is linked to lower phagocytic activity and reduction in the release of interleukine-1 by macrophages, with consequent reduction in lymphocyte stimulation, which are involved in the progression of autoimmune diseases. The compounds of the invention can therefore also be useful as immunosupressants.

Another aspect verified in the results was the presence of many colonies in the marrow stroma with erythroid characteristics, indicating stimulatory activity of said compounds over the erythroid series, which would be due to the presence of iron, which may interfere with cell metabolism.

Evaluation of Acute Toxicity

The concentration of cyclopalladated compounds of the invention as used in this study is being determined from the realization of a fixed dosage test, in which the substance to be tested is given to mice under specific dosage, which is selected from previously fixed dosages, according to classifications from ruling institutions, for which the maximum concentration to be tested should not surpass 2000 mg/kg. The benefit from the use of the fixed dosage test over $LD_{50}$ test is that, in the fixed dosage test, the evaluated standard does not necessarily need to be the death of the animal, thus minimizing suffering and the number of animals used for each experiment (Barros & Davino, 1996).

After drug administration, a 14-day observation period follows. The dosage under which signs of acute toxicity are observed, such as changes in hair, mucosa and skin, as well as the occurrence of diarrhea and convulsions, conjunctivitis, excitement or slow movements, is used to graduate or classify the tested material.

The results obtained from the protocol illustrated by Example 10 show lack of acute toxicity for the cyclopalladated compounds formed by enantiomer S(−) from dmpa with the ligand dppf under 1:1 or 1:2 proportions, as per structures A, B and C (generic structure), under doses of up to 500 and 200 mg/kg, respectively, indicating low toxicological potential and consequently less incidence of side effects. This result is particularly interesting, since the systemic toxicity of available drugs in the market frequently takes the individual to death at the start of the chemotherapeutical treatment.

In Vitro Cytotoxicity in Leukemic Lines HL-60 AND K-562 and Expression of Proto-Oncogene BCL-2:

Cytotoxicity evaluation through the method of MTT-tetrazolium (diphenyltetrazolium 3-(4,5-dimethiazol-2-il-2,5-bromide)) reduction, allowing evaluation of both cell proliferation and cytotoxicity by means of a mitochondrial oxyreduction system, was used. In this fashion, tetrazolium is reduced through viable cells, forming Formazan salt, which should be solubilized (Mosmman, 1983) to read the absorbance through ELISA at 560 nm.

From the results obtained by experiments as illustrated by Example 11, we verified cytotoxic activity of the cyclopalladated compounds in both studied lines, with results obtained from the two compounds being similar (FIGS. 10 and 11). Results show that those drugs are antileukemics, since those lines represent cells with large resistance capacity against chemotherapeuticals currently available in the market. Furthermore, one of the evaluated compounds, the cyclopalladated compound formed by the enantiomer S(−) from dmpa and the coordinated ligand dppf under 1:2 proportions, as per structure A (generic structures) was able to reduce the expression of the protein oncogene bcl-2 in leukemic cells HL60 under doses of 12.5 μg/ml, indicating that this drug induces leukemic cells to the apoptosis process, since the high expression of bcl-2 interferes with the response process to chemotherapy by means of interferences in the scheduled cell death process or apoptosis. When evaluating the morphological aspect of the cells treated with compounds containing azida, a large number of cells with necrosis characteristics (disrupted membrane and presence of cell fragments on slides) was noticed, indicating that azida compounds interfere with the oxidating metabolism, which is in agreement with the results obtained in the acute toxicity study. On the other hand, the morphological aspect of leukemic cells HL60 treated with cyclopalladated compounds is that of cells in scheduled cell death process or apoptosis, as illustrated by FIG. 12.

Biological Assays Made with Melanoma

In vitro biological assays were made to verify the cytotoxic effect of cyclopalladated compounds over murine melanoma B16F10-Nex2 cells, which were incubated with the drug for 24 hours. In vivo assays in female mice C57BI/6 were also made, in which $10^5$ tumor cells were implanted subcutaneously. After tumor implantation, the treatment started by applying a 10 μM concentration of cyclopalladated compounds intraperitoneally three times per week.

The results are presented by Example 12 and FIGS. 13, 14, 15 and 16.

Assays Made in Cell Cultures

Thyroid Tumor

Assays in thyroid tumor cell cultures from lines WRO, NPA and ARO were made. Molecular compounds of the type $[Pd(C^2,N-(S_{(-)}dmpa)(L)X]$ presented inhibiting doses ($IC_{50}$) of 0.48 μg for the line WRO, 0.59 μg for the line NPA and 0.60 μg for the line ARO. Compounds $[Pd_2(C^2,N-(S_{(-)}dmpa)_2(\mu-L)X_2]$ presented similar inhibiting doses ($IC_{50}$). For analogue cyclopalladated compounds formed by the enantiomer R(+) from dmpa, the following inhibiting doses ($IC_{50}$) were obtained: 5.56 μg for the line WRO, 6.04 μg for the line NPA and 7.57 μg for the line ARO. We again observed that, for the compounds of type $[Pd_2(C^2,N-(R_{(+)}dmpa)_2(\mu-L)X_2]$, these inhibitory doses did not change significantly. From the presented results, it became clear that, for the R(+) enantiomer, inhibiting doses $IC_{50}$ are about 10 times higher in comparison to those observed for the S(−) enantiomer. This fact shows an enantioselective dependence from the cytotoxicity process caused by the compounds, showing higher efficiency of the compounds having the S(−) isomer from dmpa in their structure.

Presented results show that such compounds can be successfully used for the therapy of thyroid cancer. These tumors are among those expressing more cathepsin D and also against which a specific and efficient chemotherapeutical is not yet available. The efficacy of the palladium complexes of the invention against said disease is even higher if we consider that those complexes also modulate the immunological system, as proven. This means that, besides giving hope for the treatment of these tumors, cyclopalladated compounds as presented herein may serve as important adjuvants for radio therapy treatments, inhibiting many of the undesirable side effects, such as leukemia, hair loss and destruction of central nervous system cells.

The cyclopalladated compounds of the invention, especially cyclopalladated compounds of the R(+) and S(−) enantiomers from N,N-dimethyl-1-phenethylamine (dmpa) and the coordinated ligand 1,1'-bis-diphenylphosphine-ferrocene (dppf), present very significant antitumor potential, particularly in leukemic lines and some melanoma lines, and may take cells to the cell apoptosis process.

The compounds of the invention present low toxicological potential and consequently less incidence of side effects and, inversely to most chemotherapeuticals, which are myelotoxic, we verified lack of myelotoxicity signs with the compounds of the invention. Results show the effects of these drugs over hematopoiesis, which is dose-dependent, and under low doses cyclopalladated compounds are less toxic for normal cells than conventional chemotherapeuticals.

When evaluating the effects of this same drug over the long-lasting liquid culture system, a response standard which has been observed with drugs inhibiting the angiotensin converting enzyme (ACE) was verified, thus resulting in the temporary interruption of the cell cycle linked to higher protection for bone marrow cells against the myelotoxic effects of conventional chemotherapy.

These results also show the activity of the compounds of the invention as immunomodulators and immunosupressants.

In these same assays, we verified that many marrow stroma colonies presented characteristics from the erythroid series, thus indicating possible stimulating activity over the erithroid series.

Dosage and Formulation

For the purposes of the invention, the recipient can be animal or human, particularly human.

The cyclopalladated compounds of the invention and compositions comprising at least one compound of the invention can be given orally by an injectable means, particularly intraperitoneally, by using any pharmaceutically acceptable dosage form known in the art for said administrations. In a particular embodiment, the compounds and compositions comprising the compounds of the invention are not changed by the digestive system, being supplied as injections.

The active ingredient can be supplied in solid dosage forms, such as dry powders, granules, tablets or capsules, or in liquid dosage forms, such as syrups or water suspensions. The administration of the compounds of the invention can also be made by e.g. but not limited to oral, subcutaneous, intravenous, intranasal, transdermal, intraperitoneal, topic, intramuscular, intralung, vaginal, rectal, intraocular or sublingual means. In some cases, the compounds can be topically applied, such as by spray or solution.

The active ingredient can be given in single form, but is generally given with a pharmaceutical carrier. An object of the invention comprises pharmaceutical compositions of which at least a cyclopalladated compound according to the presently disclosed contents makes part. An invaluable examination of the pharmaceutical dosage forms is presented by *Remington's Pharmaceutical Sciences*, Mack Publishing.

The compounds of the invention and compositions based on them can be given in oral dosage forms, such as tablets, capsules (each one of them including scheduled or prolonged release formulations), pellets, powders, granules, elixirs, essences, suspensions, syrups and emulsions. In the same fashion, they can also be given intravenously (in mixture or infusion), intraperitoneally, subcutaneously or intramuscularly, all using dosage forms well known by the experts in pharmaceutical arts. An efficient but non toxic quantity producing the desired effect of the compound can be employed to avoid or treat tumors, mainly in the combat against malignant tumors, diseases linked to tissue degradation, diseases caused by inflammatory processes and/or originated in virus, bacteria or parasite, autoimmune diseases, diabetes, amnesia, nervous and food siaoeswea, stress, alcoholism and hypertension, among others.

Dosage regimes for the compounds of the invention will naturally vary depending on known factors, such as the pharmacodynamic characteristics of the specific agent and its mode and route of administration; species, age, gender, health, medical conditions and weight of the recipient; nature and extension of symptoms; type of concurrent treatment; frequency of treatment; route of administration; general state of the recipient and desired effect. A doctor or veterinary with common knowledge can easily determine and prescribe the efficient quantity of drug as required to prevent, combat or suspend the progress of the condition.

The compounds of the invention can be advantageously given in a single daily dosage, or the full daily dosage can be given in partial doses twice, three, four times per day or more. For some treatments, however, application in alternate days is appropriate, cyclically or not.

The compounds of the invention can be given intranasally by means of the topical use of appropriate intranasal carriers or through transdermic routes, by using the kinds of transdermic skin patches well known by the experts in the art. To be given as a transdermic supply system, the dosage administration will naturally be continuous and not intermittent along the dosage regime.

For oral administration as a tablet or capsule, e.g. the active drug component can be combined with a pharmaceutically acceptable oral inert carrier, such as lactose, starch, sucrose, glucose, methyl cellulose, magnesium stearate, dicalcium phosphate, calcium sulphate, mannitol, sorbitol and similar; for oral administration in liquid forms, oral drug components can be combined with any pharmaceutically acceptable oral inert carrier, such as ethanol, glycerol, water and similar. Furthermore, when desired or required, appropriate agglutinants, lubricants, disintegrating agents and coloring agents can also be incorporated to the mixture. Appropriate agglutinants include starch, gelatin, natural sugars such as glucose or β-lactose, corn sweeteners, natural and synthetic gums such as acacia, tragacanth or sodium alginate, carboxymethylcellulose, polyethylene glycol, waxes and similar. Lubricants used in these dosage forms include sodium oleate, sodium stearate, magnesium stearate, sodium benzoate, sodium acetate, sodium chloride and similar. Disintegrants include, under no limitation, starch, methylcellulose, agar, bentonite, xanthan gum and similar.

The compounds of the invention can also be given as liposome supply systems, such as small unilamellar vesicles, large unilamellar vesicles and multilamellar vesicles. Liposomes can also be formed from a range of phospholipids, such as cholesterol, stearylamine or phosphatidilcholines.

The compounds of the invention can also be coupled to soluble polymers as possible drug carriers. These polymers can include polyvinylpyrrolidone, pyran copolymer, polyhydroxypropylmethacrylamidephenol, poly-hydroxyethylaspartamidephenol or polyethylene oxide-polylysine substituted with palmitoyl residues. Furthermore, the compounds of the invention can be coupled to a class of useful biodegradable polymers to reach the controlled release of a drug, such as polylactic acid, polyglucolic acid, copolymers of polylactic and polyglucolic acid, polyepsilon caprolactone, polyhydroxy butyric acid, polyorthoesters, polyacetals, polydihydropyrans, polycyanoacylates and crosslinked or amphypathic block copolymers of hydrogels.

Gelatine capsules can contain the active ingredient and carriers in powder, such as lactose, starch, cellulose derivatives, magnesium stearate, stearic acid and similar. Similar diluents can be used to manufacture pressed tablets. Both tablets and capsules can be manufactured in the form of delayed release products, to provide for the continuous release of the drug through many hours. Pressed tablets can be covered with sugar or film to mask any undesirable taste and protect the tablet from the atmosphere, or can be enterically covered for selective disintegration in the gastrointestinal system.

Liquid dosage forms for oral administration may contain coloring and flavoring agents to accept the recipient's acceptance. Generally, water, an appropriate oil, saline solution, water dextrose (glucose), related sugar solutions and glycols, such as propylene glycol or polyethylene glycols, phosphate buffer are appropriate carriers for liquid dosage forms, parenteral solutions or for intraperitoneal applications, besides DMSO or any coordinating solvent, a group including water.

Solutions for parenteral administration particularly contain a hydrosoluble salt of the active ingredient and DMSO, or another coordinating solvent, appropriate stabilizing agents and buffer substances, if required. Antioxidizing agents, such as sodium bisulphite, sodium sulphite or ascorbic acid, be them isolated or in combination, are appropriate stabilizing agents. Citric acid and its salts and sodium EDTA are also used. Furthermore, parenteral solutions may contain preservatives, such as benzalkonium chloride, methyl propyl paraben and chlorbutanol.

Compositions for intraperitoneal application particularly comprise water, saline solution and/or phosphate buffer pH 7.4 and 0.1 to 30% DMSO, more particularly 1 to 10% by weight of the composition and stabilizing or preservative agents, if required.

Appropriate pharmaceutical carriers are described by *Remington's Pharmaceutical Sciences*, Mack Publishing Company, a standard reference text in this field, which contents are incorporated herein.

The daily dosage of active ingredient can be expected to be about 0.0001 to about 500 mg/kg of body weight, with the particular dosage being about 0.0001 to 100 mg/kg and, more particularly, 0.0001 to about 30 mg/kg. The daily dosage can still be calculated relative to its final concentration in the volume of blood of the patient who is being supplied in order to obtain 0.01 to 200 µM, particularly 0.1 to 50 µM, more particularly from 10 to 25 µM.

Dosage forms for appropriate compositions for administration contain about 0.0001 to 250 mg, more particularly about 0.1 to 100 mg of active ingredient per unit. In these pharmaceutical compositions, the active ingredient will usually be present in a quantity of about 0.001 to 99% by weight, particularly about 0.1 to 70% and more particularly about 0.1 to 40% by weight, based on the total weight of the composition, which can also comprise at least one pharmaceutically acceptable carrier. The active ingredient can be orally given in solid dosage forms, such as capsules, tablets or powders, or in liquid dosage forms, such as elixirs, syrups, solutions and suspensions. It can also be parenterally given or intraperitoneally applied in sterile liquid dosage forms.

The preferred pharmaceutical dosage form of the invention corresponds to liquid compositions for injectable administration, particularly intraperitoneal. An appropriate parenteral formulation for administration by injection can be prepared, e.g. by means of shaking 1.5% by weight of active ingredient in 10% by volume of DMSO and phosphate buffer pH 7.4. The solution is sterilized by means of usually adopted procedures.

Dosage forms of the combination products of the invention, in which one of the active ingredients is enterically covered, may exist in the form of tablets, so that the enterically covered component and the other active ingredient are not mixed together, and subsequently pressed in a tablet or similar, so that the enterically covered component is pressed in a tablet layer and the other active ingredient is pressed in an additional layer. Optionally, so to additionally separate both layers, one or more placebo layers may be present, so that the placebo layer stays between the active ingredient layers. Furthermore, the dosage forms of the invention may exist in the form of capsules, in which one of the active ingredients is pressed in a tablet or in a number of microtablets, particles, granules or non-sphericals, which are then enterically covered. These enterically covered microtablets, particles, granules or non-sphericals are then put in a capsule or pressed in a capsule together with a granulation of the other active ingredient.

These and other forms to minimize the contact between the components of combination products of the invention, be them given in a single dosage form or given in separate forms but at the same time or simultaneously in the same fashion, will be easily clear for the experts in the art, based upon this description.

Definitions

"Hematopoyetic system" means a system related to the formation of blood cells.

"Immunological system" means a system of defense cells of the organism formed by white blood cells, directly and/or indirectly responsible to defend the organism against strange bodies of chemical or biological origin, by producing antibodies.

"Protein inhibitor" means an agent able to inhibit a protein from exerting its biological functions, generally by damages caused in its secondary and tertiary structure and/or in its active site.

"Selective inhibitor" means an inhibitor which is able to inhibit, in a large universe of molecules (e.g. proteins), only one specific molecule and/or family which has similar active sites.

"Young cell cycle" means the cyclic structural and biochemical facts occurring during the quick growth of cells, such as in tissue culture. The cycle is divided into periods called $G_0$, Hiatus$_1$ ($G_1$), synthesis (S), Hyatus$_2$ ($G_2$) and Mitosis (M). When occurring e.g. with a myelomonocyte, a young cell from the granulocytic series, it is referred to as young cell cycle.

"Myelosuppression" means the suppression of myelocite production, i.e. young cells from the granulocytic series, usually occurring in the bone marrow, but not in the circulating blood (except for some diseases).

"Myelotoxicity" means the action of an agent able to cause toxicity in bone marrow cells.

"Autoimmune diseases" mean every disease caused when the defense cells from the immunological system of the organism do not recognize the own normal cells from the organs and/or tissues constituting it.

"Immunosupressant" means every agent able to cause immunosuppression, i.e. prevention or interference with the development of the immunological response; it can be a consequence of lack of immunological response (tolerance), can be artificially induced by chemical, biological or physical agents or can be caused by a disease.

"Immunomodulator" means every agent able to cause functional and morphological fluctuation of cells from the immunological system in response to changes in the environmental conditions of the cells.

"Chelating biphosphinic ligand" means every organic linker containing two atoms of phosphorous with free electronic pairs linking to a same metal center by donating coordinate links.

"DNA insertion" means the coordination of a chemical molecule between a pair of basis forming double helix of the DNA molecule.

"Analogous linker" means all isostructural linkers, i.e. with similar geometrical structure. In the invention, any element from the group V of the periodic table of chemical elements linked at the cyclopentadienyl rings of 1,1'-bis-diphenylphosphine-ferrocene in substitution to the atom of phosphorous, and it may be N, As, Sb or Bi.

"Total volume of recipient blood" means the total volume of blood circulating in the organism of the recipient. Considering human beings, this volume varies between six and eight liters.

As the experts in the art will realize, numerous modifications and variations of the invention are possible in the light of the above teachings. It should therefore be understood that, within the scope of the attached claims, the invention can be embodied in other ways besides those specifically described herein.

Merely illustrative examples of specific embodiments of the invention are presented below, not creating any limitations to its scope aside from those contained in the attached claims.

EXAMPLE 1

Preparation of Starting Complexes

[Pd($C^2$,N-dmpa)μ-Cl]$_2$; dmpa=R(+) and S(−) enantiomers of N,N-dimethyl-1-phenethylamine (dmpa) prepared according to Ryabov et al (*Reaction paths in the cyclopalladated NN-dialkylbenzylamine-substituted styrene system in acetic acid as solvent. The structure of palladated 2-dialkylaminomethylstilbenes. J. Chem. Soc., Perkin Trans;* 1983, 2, 1503-1509) and (*Enantioselective cleavage of activated amino acid esters promoted by chiral palladacycles. Inorg. Chim. Acta;* 1988, 280, 57-61). % analysis (calcd. $C_{20}H_{28}N_2Cl_2Pd_2$): a) R(+): C, 40.4 (40.6); H 4.8(4.7); N, 4.8 (4.4). b) S(−): C, 40.4 (40.9); H, 4.8 (4.2); N,4.8 (4.3).

[Pd($C^2$,N-dmpa)μ-$N_3$]$_2$—These compounds were prepared from R(+) and S(−) dimer enantiomers from [Pd($C^2$,N-dmpa)P-Cl]$_2$ by means of an ion exchange reaction. To a solution of [Pd($C^2$,N-dmpa)μ-Cl]$_2$ (1.740 g, 3.0 mmol) in THF (100 mL), a $NaN_3$ solution (0.390 g, 6.00 mmol) in methanol (20 mL) was added. The yellow solid obtained was filtered, washed with $Et_2O$ and dried under vacuum. Recristallization from toluene formed microcrystalline products (95% R(+); 87% S(−)). % analysis (calcd. $C_{20}H_{28}N_8Pd_2$): a) R(+): C, 40.6 (40.2); H, 4.7 (4.4); N, 18.9 (18.3). IR: vas$N_3$ 2066 cm$^{-1}$, vsim$N_3$ 1447 cm$^{-1}$ b) S(−): C, 40.6 (41.1); H, 4.7 (4.5); N, 18.9 (18.4). IR: vas$N_3$ 2058 cm$^{-1}$, vsim$N_3$ 1443 cm$^{-1}$.

EXAMPLE 2

Ionic Compounds Presenting Chelated Biphosphinic

Ligands of the Type PD($C^2$,N-DMPA)(L)]X(X=CL, $N_3$, L=Bidentated Ligand)

Remark: These compounds appear sometimes in the descriptive texts as: Pd R(+) or S(−) dmpa dppf 1:2 (with $N_3$ or Cl).

(2a) [Pd($C^2$,N-(R+dmpa)(dppf)]$N_3$

% analysis (calcd.): C, 60.9 (62.1); H, 4.8 (5.0), N, 6.1 (6.6). $^1$H-NMR (ppm): —CH—$CH_3$* (6H, d, 1.55); —N($CH_3$)$_2$ (3H, s, 2.16); Cp (5H, m, 3.99) Cp (5H, m, 4.25)— CH*—$CH_3$ (2H, q, 3.99); H-aromatic ring 35). $^{31}$P{$^1$H}-NMR (ppm): 2 signals: 23.0, 32.1. ΛM=44.5 S.cm$^2$.mol$^{-1}$.

[Pd($C^2$,N-(R+dmpa)(dppf)]Cl (same).

(2b) [Pd($C^2$,N-(S-dmpa)(dppf)]$N_3$

% analysis (calcd.): C, 61.9 (62.1); H, 5.5 (5.0), N, 5.9 (6.6). $^1$H-NMR (ppm): —CH—$CH_3$* (6H, d, 1.55); —N($CH_3$)$_2$ (3H, s, 2.16); Cp (5H, m, 4.21) Cp (5H, m, 4.49) —CH*—$CH_3$ (2H, q, 3.97); H-aromatic ring (24, m, 7.25-7.32. $^{31}$P{$^1$H}-NMR (ppm): 2 signals: 23.0, 32.1. ΛM=51.1 S.cm$^2$.mol$^{-1}$.

[Pd($C^2$,N-(S-dmpa)(dppf)]Cl (same).

EXAMPLE 3

Molecular Compounds Presenting Chelated

Biphosphinic Ligands of the Type
[PD(C2,N-DMPA)(L)]X (X=CL, $N_3$, L=Bidentated

Ligand)

Remark: These compounds appear sometimes in the descriptive texts as: Pd R(+) or S(−) dmpa dppf 1:2 (with $N_3$ or Cl).

(3a) [Pd($C^2$,N-(R+dmpa)(dppf)$N_3$]
% analysis (calcd.): C, 61.3 (62.1); H, 4.9 (5.0), N, 6.1 (6.6). $^1$H-NMR (ppm): —CH—$CH_3$* (6H, d, 1.55); —N$(CH_3)_2$ (3H, s, 2.16); Cp (5H, q, 3.99) Cp (5H, t, 4.25)—CH*—$CH_3$ (2H, q, 3.77); H-aromatic rings (24, m, 7.25-7.32). $^{31}$P{$^1$H}-NMR (ppm): 2 signals: 31.9; −16.0. ΛM=15.5 S.cm$^2$.mol$^{-1}$.
[Pd($C^2$,N-(R+dmpa)(dppf)Cl] (same).

(3b) [Pd($C^2$,N-(S-dmpa)(dppf)$N_3$]
% analysis (calcd.): C, 61.9 (62.1); H, 4.5 (5.0), N, 5.9 (6.6). $^1$H-NMR (ppm): —CH—$CH_3$* (6H, d, 1.55); —N$(CH_3)_2$ (3H, s, 2.16); Cp (5H, q, 3.99) Cp (5H, t, 4.25)—CH*—$CH_3$ (2H, q, 3.77); H-aromatic rings (24, m, 7.25-7.32). $^{31}$P{$^1$H}-NMR (ppm): 2 signals: 31.9; −16.0. ΛM=13.2 S.cm$^2$.mol$^{-1}$
[Pd($C^2$,N-(S-dmpa)(dppf)Cl] (same).

EXAMPLE 4

Molecular Compounds Presenting Chelated

Biphosphinic Ligands of the Type [PD$_2$($C^2$,N-DMPA)$_2$(μ-L)X$_2$] (X=CL, $N_3$, L=Bidentated Ligand)

Remark: These compounds appear sometimes in the descriptive texts as: Pd R(+) or S(−) dmpa dppf 1:1 (with $N_3$ or Cl).

(4a) [Pd$_2$($C^2$,N-S-dmpa)$_2$(μ-dppf)Cl$_2$]
% analysis (calcd.): C, 56.7 (57.1); H, 5.2 (5.0), N, 2.4 (2.5). $^1$H-NMR (ppm): —CH—$CH_3$* (6H, d, 2.60); CH—$CH_3$* (6H, d, 2.90); —N$(CH_3)_2$ (6H, s-br, 1.61); -N$(CH_3)_2$ (6H, s-br, 1.63); P$(CH_2)_2$—P (4H, m, 2.57-2.85); Cp (2H, sr-br, 4.23), Cp (2H, sr-br, 4.57), Cp (3H, m, 4.96), Cp (3H, m, 5.00), —CH*—$CH_3$ (2H, q, 4.10); H-aromatic rings (24, m, 6.25-7.57. $^1$P{$^1$H}-NMR (ppm): 1 signal: 32.7. ΛM=9.3 S.cm$^2$.mol$^{-1}$.
[Pd$_2$($C^2$,N-S-dmpa)$_2$(μ-dppf)($N_3$)$_2$] (same).

(4b) [Pd$_2$($C^2$,N-R+ dmpa)$_2$(μ-dppf)Cl$_2$]
% analysis (calcd.): C, 54.3 (57.1); H, 4.9 (5.0), N, 2.3 (2.5). $^1$H-NMR (ppm): —CH—$CH_3$* (6H, d, 2.60); CH—$CH_3$* (6H, d, 2.90); —N$(CH_3)_2$ (6H, s-br, 1.61); -N$(CH_3)_2$ (6H, s-br, 1.63); P$(CH_2)_2$—P (4H, m, 2.57-2.85); Cp (2H, sr-br, 4.23), Cp (2H, sr-br, 4.57), Cp (3H, m, 4.96), Cp (3H, m, 5.00), —CH*—$CH_3$ (2H, q, 4.10); H-aromatic rings (24, m, 6.25-7.57. $^{31}$P{$^1$H}-NMR (ppm): 1 signal: 32.7. ΛM=2.4 S.cm$^2$.mol$^{-1}$.
[Pd$_2$($C^2$,N-R+ dmpa)$_2$(μ-dppf)($N_3$)$_2$] (same).

(4c) [Pd$_2$($C^2$,N-S-dmpa)$_2$(μ-dppf)($N_3$)$_2$]
% analysis (calcd.): C, 55.1 (55.9); H, 4.0 (4.5), N, 9.5 (10.0). $^1$H-NMR (ppm): —CH—$CH_3$* (6H, d, 2.70); CH—$CH_3$* (6H, d, 3.00); —N$(CH_3)_2$ (6H, s-br, 1.61); —N$(CH_3)_2$ (6H, s-br, 1.65); P$(CH_2)_2$—P (4H, m, 2.60-2.90); Cp (2H, sr-br, 4.20), Cp (2H, sr-br, 4.61), Cp (3H, m, 4.93), Cp (3H, m, 5.10), —CH*—$CH_3$ (2H, q, 4.20); H-aromatic rings (24, m, 6.05-7.77 $^{31}$P{$^1$H}-NMR (ppm): 1 signal: 32.7.ΛM=7.5 S.cm$^2$.mol$^{-1}$.
[Pd2($C^2$,N-S-dmpa)$_2$(μ-dppf)Cl$_2$] (same).

(4d) [Pd$_2$($C^2$,N-R+ dmpa)$_2$(μ-dppf)($N_3$)$_2$]
% analysis (calcd.): C, 54.8 (55.9); H, 4.1 (4.5), N, 9.7 (10.0). $^1$H-NMR (ppm): —CH—$CH_3$* (6H, d, 2.70); CH—$CH_3$* (6H, d, 3.00); —N$(CH_3)_2$ (6H, s-br, 1.61); —N$(CH_3)_2$ (6H, s-br, 1.65); P$(CH_2)_2$—P (4H, m, 2.60-2.90); Cp (2H, sr-br, 4.20), Cp (2H, sr-br, 4.61), Cp (3H, m, 4.93), Cp (3H, m, 5.10), —CH*—$CH_3$ (2H, q, 4.20); H-aromatic rings (24, m, 6.05-7.77). $^{31}$P{$^1$H}-NMR (ppm): 1 signal: 32.7. ΛM=4.4 S.cm$^2$.mol$^{-1}$.
[Pd$_2$($C^2$,N-R+ dmpa)$_2$(μ-dppf)Cl$_2$] (same).

EXAMPLE 5

Enzymatic Inhibition Assays with the Family of

Serine Peptidase, Metallo-Proteinase Enzymes

We include below assays made with the complexes with structures A, B and C. These palladium complexes are constituted by the cyclometal ring formed by the R(+) and S(−) isomers of N,N-dimethyl-1-phenethylamine (dmpa) and by the coordinated ligand 1,1'-bis-diphenylphosphine-ferrocene (dppf). Enzymatic inhibition constants were obtained by classical methods, by using spectrofluorimetry skills and indirect calculations. In the assays, 1 ml volumes of enzyme solutions were used, containing a known total; mass from 2 to 5 ng, depending on the assay. The following Enzymatic Inhibition Constant values listed below were calculated:

Serine Peptidase:

Prolyl oligopeptidase (POP) and two variants (one Cys255The mutant from the fourth blade of the beta-propeller and the functional mutant Tyr473Phe). For POPs, the used buffer was Tris/HCl 20 mM, pH 7.5. Standard substrate was Abz-GFSPFRQ-EDDnp (Km 0.38 μM).

(5a) Complexes with the R(+) Isomer from dmpa (in 1:1 Structures):
:$1/K_{iapp}$=0.0977//$K_{iapp}$=10.24 ng//Ki=4.51 ng for the mutant Cys255The.
:$1/K_{iapp}$=0.1234//$K_{iapp}$=8.10 ng//Ki=3.57 ng for the mutant Tyr473Phe.

(5b) Complexes with the R(+) Isomer from dmpa (in 2:1 Structures)
:$1/K_{iapp}$=8.7242//$K_{iapp}$=0.1146 ng//Ki=34.01 pg, for the mutant Cys255The.
:$1/K_{iapp}$=14.1677//$K_{iapp}$=0.0706 ng//Ki=20.94 pg, for the mutant Tyr473Phe.

(5c) Complexes with the S(−) Isomer from dmpa (in 1:1 Structures):
:$1/K_{iapp}$=6.9164//$K_{iapp}$=0.1496 ng//Ki=42.90 pg, for the mutant Cys255The.
:$1/K_{iapp}$=9.8914//$K_{iapp}$=0.1011 ng//Ki=30 pg, for the mutant Tyr473Phe.

(5d) Complexes with the S(−) Isomer from dmpa (in 2:1 Structures):
:$1/K_{iapp}$=180.3018//$K_{iapp}$=0.004982 ng//Ki=1.65 pg, for the mutant Cys255The.
:$1/K_{iapp}$=4.4990//$K_{iapp}$=0.2223 ng//Ki=65.96 pg, for the mutant Tyr473Phe.

Metallo-Protease:

ACE (angiotensin converting enzyme)—used concentration: 0.1-1.0 nM. The used buffer was buffer sodium phosphate 0.1 M, pH 8.0+200 mM NaCl. The standard substrate was Abz-YRK(Dnp)-P—OH (Km: 7.0 μM).

(5e) Complexes with the R(+) Isomer from dmpa (in 1:1 Structures)
:$1/K_{iapp}$=18.7138//$K_{iapp}$=0.05344 ng//Ki=22.27 pg.

(5f) Complexes with the R(+) Isomer from dmpa (in 2:1 Structures)
:$1/K_{iapp}$=1.1578//$K_{iapp}$=0.8637 ng//Ki=0.36 ng.

(5g) Complexes with the S(−) Isomer from dmpa (in 1:1 Structures)
:$1/K_{iapp}$=2.0989//$K_{iapp}$=0.4764 ng//Ki=198.51 pg.

(5h) Complexes with the S(−) Isomer from dmpa (in 2:1 Structures)

$1/K_{iapp}=3.3136//K_{iapp}=0.3018$ ng//Ki=112.28 pg.

Endopeptidase:

CATD (Cathepsin D)—used concentration: 0.05-0.5 nM. The used buffer was the buffer sodium citrate 0.1 mM, pH 4.0. Standard substrate was Abz-AIAFFSRQ-EDDnp (Km 0.17 µM).

(5i) Complexes with the S(−) Isomer from dmpa (in 1:1 Structures)

:$1/K_{iapp}=3.3136//K_{iapp}=0.3018$ ng//Ki=122.98 pg.

(5j) Complexes with the S(−) Isomer from dmpa (in 2:1 Structures)

:$1/K_{iapp}=3.5696//K_{iapp}=0.2801$ ng//Ki=104.22 pg.

EXAMPLE 6

Antitumor Assay—Walker's Tumor

For the antitumoral action assay, the compounds were diluted in water solution, saline solution and phosphate buffer solution with pH=7.4, all of them containing 1% dimethyl-sulfoxide (DMSO). Applications of equivalent quantities of the compounds were made, so that their concentration in the total volume of blood of the test animal (estimated at 30 ml) totals drug concentration of 15 µM in the living organism, which is considered very good for kinetic steps.

Experiments were made with intraperitoneal, subcutaneous and direct application on the region of tumor implantation and also by tumor implantation, through tumor cells, together with the palladium compounds of the invention.

It was noticed that the tumor growth can be reverted in 90% of the cases (total of 60 test animals). Subcutaneous inoculations of $10^6$ tumor cells develop solid tumors with mass of 4.0 (+/−) 1.0 g in the test animal after twelve days. With the application of the drug, this mass is reduced to 0.3 (+/−) 0.1 g. Besides inhibiting tumor development, the compounds reverted previously existent tumors in 85% of the cases. For the Walker's tumor as mentioned, the compound presented in the in vivo model selective cytotoxicity for tumor cells, with no chronic signals of inflammation when the drug was applied over normal tissues. In these assays, injections of 15 µM/rat× day were applied for 10 (ten) consecutive days. Another important action was the inhibitory effect over endothelial cell proliferation in culture, showing an important antiangiogenic action. The compounds also presented in the in vivo model large inhibitory action over Cathepsin B and over Cathepsin D, being an effective antimetastasis agent, avoiding tumor metastasis in the skeleton muscle.

The fact that no side effects were observed in none of the animal tests by any treatment must be highlighted, thus revealing high drug specificity. FIGS. 3, 4 and 5 below show some of the obtained results.

EXAMPLE 7

To develop the Ehrlich's ascitic tumor, mice are intraperitoneally inoculated with 0.1 ml of a suspension of tumor cells containing $10^6$ cells, originating from the peritoneal cavity of holder mice. After taking out the ascitic liquid from the peritoneum of mice holding the tumor of Ehrlich, the number and viability of cells are determined by using trypan blue colorant in a Neubauer chamber.

With the purpose to observe possible protection of treated animals with the compounds [$Pd_2(C^2,N$-S-dmpa$)_2(\mu$-dpp)$Cl_2$] e [$Pd_2(C^2,N$-S-dmpa$)_2(\mu$-dppf)$(N_3)_2$] (as per scheme C shown in generic structures), a life extension curve was made.

Three experimental groups of twelve animals were considered as follows: animals holding only the ascitic tumor of Ehrlich; holding the tumor and treated with four consecutive doses of the cyclopalladated compounds (1 mg/kg) subcutaneously.

This experiment was made as follows:

Cells of tumor of Ehrlich were removed from the peritoneal cavity of holder animals and then diluted (1:100) in a trypan blue solution to determine cell viability. The concentration was adjusted in saline for $1\times10^6$ cells/animal. Then, 0.2 ml of this solution (containing $1\times10^6$ cells) were inoculated in the animals being studied. Seventy-two hours after tumor inoculation, treatment with cyclopalladated compounds was started and kept for four consecutive days. The animals were daily observed to control mortality.

In in vivo assays, both the compound [$Pd(C^2,N$-(S-dmpa)(dppf)Cl] and [$Pd_2(C^2,N$-S-dmpa$)_2(\mu$-dppf)$(N_3)_2$], under the dose of 1 mg/kg, increased the life extension of animals holding the ascitic tumor of Ehrlich, indicating that these drugs are able to interfere with tumor progression (FIG. 6).

EXAMPLE 8

Clonal Culture of Hematopoietic Precursors from the Bone Marrow of Mice (CFU-C)

To count these clogenical cells, it is important that all multipotential cells present in the culture are induced to proliferate and the culture conditions are adjusted, so to avoid a too high number of colonies on each Petri plate with their consequent superposition, so to allow the identification of each colony. It is also important that the growth-stimulating factor (GSF) is used above maximum concentrations. We will use the recombinant hematopoietic growth factor for granulocytes and macrophages—GM-CSF. Furthermore, the choice of phoetal bovine sorum should be carefully made, due to the variation found for the activity of various batches and trademarks available in the market.

After sacrificing normal mice or treated with the cyclopalladated compound formed by dmpa and the ligand dppf under 1:2 proportion (as per schemes A and B—generic structures) subcutaneously for four consecutive days, by means of cervical displacement, the skin is cleaned with iodinized alcohol. After exposing the femur, the cartilage over the orifice on the distal end is removed and the bone is cut at the upper junction. Bone marrow is transported with the help of a needle and syringe to a tube containing culture medium or balanced saline solution. The number of cells in the suspension is counted in a hemacytometric chamber after 1:10 dilution of cells in 10% eosine. Subsequently, the more agar medium is prepared (bacto-agar, Difco), consisting of 30% 2-time concentrated IMDM medium (Sigma), 20% phoetal bovine sorum and 50% agar (0.6%). Subsequently, the appropriate volume of cells is added when the more agar medium is at 37° C. Cells are re-suspended and 1.0 ml volumes are distributed over each Petri plate, which already contain the appropriate stimulus. In in vitro assays, serial concentrations of the cyclopalladated compounds formed by dmpa and the ligand dppf under 1:2 proportion (as per schemes A and B—generic structures) were added. The content is distributed throughout the surface of the Petri plate and is allowed to gel. It is incubated for seven days at 37° C. in the presence of 5% $CO_2$ in the air and the number of colonies is subsequently counted in a dissection microscope with 40× magnification (Metcalf, 1984).

EXAMPLE 9

Evaluation of the Formation of Marrow Stroma by Means of the Long-Lasting Bone Marrow Cell Liquid Culture Procedure:

This culture is fully dependent on the formation of a layer of adhering cells, derived from stromal cells of the bone marrow. The formation of this layer of adhering cells occurs by synthesis and secretion of hematopoietic growth factors, which are responsible for the formation of the extracellular matrix of stromal cells. Thus, more immature cells remain inside that layer of adhering cells and are released to the culture medium, with the aim to keep hematopoiesis. Therefore, the number of progenitor cells in the liquid culture medium is quantified after effecting clonal culture, in the presence of exogen hematopoietic growth factors (Spooncer et al, 1993).

After sacrificing the animals (about eight) by cervical displacement, femurs were exposed and the bones on the upper junction were incised. Bone marrow and marrow stroma cells were transported with the help of a needle and syringe to a tube containing culture medium rpmi-1640 (Sigma) supplemented with 2 mm l-glutamine, 20% horse sorum (cult-lab) and $10^{-2}$ M hydrocortisone. The volume of cells plus medium was distributed in culture flasks (t25) (10 ml of medium plus cells in each flask). Subsequently, culture flasks were incubated in a wet oven with 5% $CO_2$ in air. After 15 days, a new cell population derived from the bone marrow of eight mice was added to the culture flasks to induce proliferation of progenitor cells, since marrow stroma was already starting confluence. We then made, 15 days after re-population of the culture flasks, the clonal culture (cfu-c) with the aim to quantify the number of hematopoietic precursors produced by adhering cells derived from the marrow stroma cultivated in vitro. To quantify the number of non-adhering and progenitor cells, every week 50% of the saturated medium are removed and fresh medium is added, which should already contain 1 mg/l of the cyclopalladated compound formed by dmpa and the ligand dppf under 1:2 proportion (as per schemes A and B—generic structures).

Clonal Culture of Hematopoietic Precursors (CFU-C)

from Progenitor Cells Obtained in the Long-Lasting Liquid

Culture Medium

After obtaining non-adhering cells from the long-lasting liquid culture system, these were washed in medium RPMI 1640 (Sigma) and re-suspended at final concentration of $2 \times 10^5$ cells/ml. These cells were subsequently submitted to the clonal culture protocol (CFU-C) as described in the previous item.

EXAMPLE 10

Evaluation of Acute Toxicity

Assayed compounds are diluted in saline containing 10% DMSO and then 0.2 ml of that solution are intraperitoneally given to the animals. Therefore, groups of 10 animals (5 males and 5 females) were treated with various doses of the compounds being studied. The control animals received only saline with 10% DMSO. After the end of the treatment, the animals remained in observation for a period of 14 days.

TABLE 1

Evaluation of acute toxicity of cyclopalladated compounds. The animals received one dose of the compounds described below intraperitoneally and were observed for a 14-day period after this procedure.

| Cyclopalladated compounds | Doses (mg/kg) | Signs and symptoms |
|---|---|---|
| S(⁻)dmpa Cl⁻ dppf (1:2) [Pd($C^2$,N-(S-dmpa)(dppt) Cl] [Pd($C^2$,N-(S-dmpa)(dppt)]Cl | 50 and 200 | Lack of acute toxicity signs |
| R(⁺)dmpa $N_3$ dppf (1:2) [Pd($C^2$,N-(R+ dmpa)(dppf)$N_3$] [Pd($C^2$,N-(R+ dmpa)(dppf)]$N_3$ | 10 | Signs of conjunctivitis. |
| R(⁺)dmpa Cl⁻ dppf (1:1) [$Pd_2$($C_2$,N-R+ dmpa)$_2$(μ-dppf) Cl2] | 10 | Signs of conjunctivitis and hair erection. |
| S(⁻)dmpa Cl⁻dppf (1:1) [$Pd_2$($C_2$,N- S- dmpa)$_2$(μ-dppf)Cl2] | 500 | Lack of acute toxicity signs |

Compounds containing azida are toxic under the dosage of 10 mg/kg with mortality rate of 10%, indicating higher rate of side effects for this drug.

EXAMPLE 11

In Vitro Cytotoxicity in Leukemic Lines HL-60 and K-562 and Expression of Proto-Oncogene BCL-2:

Cells from cell lines HL-60 and K-562 maintained in medium RPMI-1640 (Sigma) supplemented with 2 mM L-glutamine and 20% phoetal bovine sorum were previously washed (three times) and re-suspended in RPMI medium. Subsequently, they were incubated with nine concentrations of the compounds being studied (160, 80, 40, 20, 10, 5, 2, 5, 1, 25 and 0.65 µg/ml) on a 96-orifice culture plate ($1 \times 10^6$ cells/orifice). They were then incubated in a wet oven (5% $CO_2$ in air) for 72 hours. After this period, MTT solution (5 mg/ml) (Sigma) was added and the culture plate was incubated for other four hours. Subsequently, the stabilizing MTT solution (0.04 N isopropylic acid) was added and, after 30 minutes, ELISA reading was made at 560 nm in three copies (Mosmann, 1983). Cell survival percentage in the presence of the compounds being studied was calculated as follows:

$$\% \text{ Viable cells} = \frac{\text{Absorbance per orifice (with drug)} \times 100}{\text{absorbance of the control (without drug)}}$$

EXAMPLE 12

Biological Assays Made with Melanoma

In Vitro Assays

In vitro assays were made to verify the cytotoxic effect of cyclopalladated compounds of murine melanoma B16F10-Nex2 cells. The cells were incubated for 24 hours under different concentrations. Cell viability was determined by an assay with MTT. As shown in FIG. 13, 100% efficiency is observed under concentration about 1.25 µM of the drugs containing ethane biphosphine (drugs 1, 2 and 3). The same efficiency is noted in the drug containing bis-diphenylphosphine-ferrocene, but under higher concentration, 10 µM (drug 6) and for cyclopalladated compounds containing functionalized alkenes derived from functionalized alkynes (drug 10), about 20 μM. FIG. 13 shows the described cytotoxic effect, in which the reduction percentuals of cell viability, in comparison to a control with cells with no drugs, are represented over the bars.

In Vivo Assays

In vivo assays were made in female mice C57BI/6. $10^5$ tumor cells were implanted subcutaneously. Four days after the implantation, the treatment of the animals started. One group received 10 μM and the other one received 30 μM of the most efficient drugs as follows: drugs 1, 2, 3, 6 and 10 interperitoneally, three times per week and, on these days, tumor volumes were quantified. The animals were sacrificed when the tumor volume reached 3000 $mm^3$. In the figures below, mortality curves for animals injected with drugs and control animals on (A) and, on (B), tumor volumes of animals developing tumors in each group.

In FIG. 14, from the drugs given under 10 μM concentration, a life extension of ten days is observed on A for animals treated with drugs 1, 3, 6 and 10. On B, we can notice that, from all drugs, drugs 1 and 6 were those presenting inhibitory effect to the tumor development of about 60% over other drugs.

In FIG. 15, from the drugs given under 30 μM concentration, a life extension of about seven days is observed on A for animals treated with all drugs and the group treated with the drug 6 reached lower number of deaths. In Figure B, we can see the drug 1 as the most efficient to inhibit tumor development. Drug 6, with 18 days, presents significant inhibitory effect, but this effect is inverted after 23 days.

Drugs with functionalized alkenes derived from functionalized alkynes were also tested in vitro (FIG. 16) following the same protocol and presented cytotoxic effect of 100%, about 100 μM. This effect is represented in the following figure, also showing that, among them, drugs 11 and 14 presented significant inhibition from 40 to 50%, about 1 μM.

Result analysis offers some important co-relations between chemical structure and drug activity. 100% efficiency is observed under a concentration of about 1.25 μM of the drugs containing ethane biphosphine (drugs 1, 2 and 3). The same does not occur for cyclopalladated compounds containing functionalized alkenes derived from functionalized alkynes (drug 10), in which a concentration about 20 μM is required. From all tested drugs, we can notice that drugs 1 and 6 were those presenting an inhibitory effect over tumor development of about 60% over other drugs. We can see the drug 1 as being the most efficient one to inhibit tumor development, but test animals treated with drug 6 present a lower number of deaths. From the complexes containing functionalized alkenes, drugs 11 and 14 are those presenting significant inhibition, from 40 to 50%, of about 1 μM.

It will be appreciated that the description of the invention presented herein, as well as the described examples, allow the expert in the art to embody the invention, including amendments within his or her common knowledge, without escaping from the scope of the invention as expressed in the attached claims.

What is claimed is:

1. A cyclopalladated compound, which is an organometallic compound comprising palladium, a Sigma C—Pd bond and a coordination bond Y→Pd, originating an organic cycle with formula corresponding to the structure below:

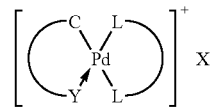

wherein:

X represents an element chosen from the group consisting of: halogen;

pseudo-halogen and acetate; and

Y is a nitrogen atom (N) within a moiety selected from the group consisting of N,N-dimethyl-1-phenethylamine (dmpa), pyridinyl-phenyl-ethyne, 1-phenyl-3-N,N-dimethylamine-propyne;

C is selected from the group consisting of a carbon atom at the ortho position of the dmpa, a carbon atom within the pyridinyl-phenyl-ethyne, a carbon atom within the 1-phenyl-3-N,N-dimethylamine-propyne; and the carbon atom is covalently bonded to the atom of palladium; the ring containing C, Y and Pd can be constituted of three to eight atoms;

between C and Y, represented by a curved line, there is a succession of atoms designated as a cyclopalladated ring;

L represents a coordinated ligand which is a donating atom from group V of the Periodic Table (N, P, As, Sb, Bi) within a bis-diphenylphosphine-ferrocene compound as detailed by Scheme 2 below, with the schematic representation L-L indicating the presence of two linkers L within the structure of said bis-diphenylphosphine-ferrocene compound, while R1 and R2 are each phenyl groups, and R3, R4, R5, R6, R7, R8, R9, R10, R11 and R12 are individually selected from the group consisting of the following radicals, which can be present in any order: hydrogen (H), alkyl, aryl, dienyl, alkoxy, siloxy, hydroxy (OH), amine (—NH2), imide, halogen (F, Cl, Br, I), imine, and nitro (—NO2);

SCHEME 2

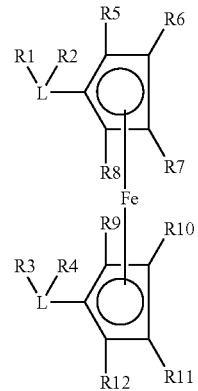

or a pharmaceutically acceptable salt or adduct of the cyclopalladated compound.

2. The cyclopalladated compound of claim 1 wherein X is selected from the group consisting of Cl, F, Br, I, $N_3$, NCO, NCS, an SCN.

3. The cyclopalladated compound of claim 1 wherein X is Cl.

4. The cyclopalladated compound of claim 1 wherein Y is the nitrogen atom within the dmpa and C is the carbon atom at the ortho position of the dmpa.

5. The cyclopalladated compound of claim 1 wherein L is P.

6. The cyclopalladated compound of claim 1 wherein R5, R6, R7, R8, R9, R10, R11, and R12 are each a hydrogen.

* * * * *